(12) United States Patent
Izadyyazdanabadi et al.

(10) Patent No.: US 12,131,461 B2
(45) Date of Patent: Oct. 29, 2024

(54) SYSTEMS, METHODS, AND MEDIA FOR AUTOMATICALLY TRANSFORMING A DIGITAL IMAGE INTO A SIMULATED PATHOLOGY IMAGE

(71) Applicants: DIGNITY HEALTH, San Francisco, CA (US); Arizona Board of Regents on behalf of Arizona State University, Scottsdale, AZ (US)

(72) Inventors: Mohammadhassan Izadyyazdanabadi, Tempe, AZ (US); Mark C. Preul, Scottsdale, AZ (US); Evgenii Belykh, Phoenix, AZ (US); Yezhou Yang, Phoenix, AZ (US)

(73) Assignees: DIGNITY HEALTH, San Francisco, CA (US); ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 579 days.

(21) Appl. No.: 17/310,305

(22) PCT Filed: Jan. 28, 2020

(86) PCT No.: PCT/US2020/015332
§ 371 (c)(1),
(2) Date: Jul. 27, 2021

(87) PCT Pub. No.: WO2020/159935
PCT Pub. Date: Aug. 6, 2020

(65) Prior Publication Data
US 2022/0051400 A1 Feb. 17, 2022

Related U.S. Application Data

(60) Provisional application No. 62/797,784, filed on Jan. 28, 2019.

(51) Int. Cl.
*G06T 7/00* (2017.01)
*A61B 1/00* (2006.01)
(Continued)

(52) U.S. Cl.
CPC .......... *G06T 7/0012* (2013.01); *A61B 1/0005* (2013.01); *A61B 1/063* (2013.01);
(Continued)

(58) Field of Classification Search
CPC ......... G06T 7/0012; G06T 2207/10056; G06T 2207/10068; G06T 2207/20084;
(Continued)

(56) References Cited

U.S. PATENT DOCUMENTS 8,488,863 B2 * 7/2013 Boucheron ........... G06T 7/0012
382/133
11,756,675 B2 * 9/2023 Orringer ............... G06T 7/0012
(Continued)

FOREIGN PATENT DOCUMENTS

| WO | WO-2017023569 A1 * | 2/2017 | .......... A61B 5/0042 |
| WO | 2018/152248 A1 | 8/2018 | |
| WO | 2018/19333 A1 | 10/2018 | |

OTHER PUBLICATIONS

"Noha Ghatwary et al., In-vivo Barretts Esophagus Digital Pathology Stage Classification through Feature Enhancement of Confocal Laser Endomicroscopy, Jan. 1, 2019, Journal of Medical Imaging, vol. 65, Issue 1" (Year: 2019).*

(Continued)

*Primary Examiner* — Andrae S Allison
*Assistant Examiner* — Phuong Hau Cai
(74) *Attorney, Agent, or Firm* — QUARLES & BRADY LLP

(57) ABSTRACT

In accordance with some embodiments of the disclosed subject matter, systems, methods, and media for automatically transforming a digital image into a simulated pathology image are provided. In some embodiments, the method comprises: receiving a content image from an endomicroscopy device; receiving, from a hidden layer of a convolu-
(Continued)

tional neural network (CNN) trained to recognize a multitude of classes of common objects, features indicative of content of the content image; receiving, providing a style reference image to the CNN; receiving, from another hidden layer of the CNN, features indicative of a style of the style reference image; receiving, from the hidden layers of the CNN, features indicative of content and style of a target image; generating a loss value based on the features of the content image, the style reference image, and the target image; minimizing the loss value; and displaying the target image with the minimized loss.

20 Claims, 10 Drawing Sheets

(51) Int. Cl.
    *A61B 1/06*     (2006.01)
    *A61B 1/313*     (2006.01)
    *A61B 90/20*     (2016.01)
    *G06N 3/045*     (2023.01)

(52) U.S. Cl.
    CPC .............. *A61B 1/313* (2013.01); *A61B 90/20* (2016.02); *G06N 3/045* (2023.01); *G06T 2207/10056* (2013.01); *G06T 2207/10068* (2013.01); *G06T 2207/20084* (2013.01); *G06T 2207/30016* (2013.01); *G06T 2207/30096* (2013.01)

(58) Field of Classification Search
    CPC . G06T 2207/30016; G06T 2207/30096; G06T 11/001; A61B 1/0005; A61B 1/063; A61B 1/313; A61B 90/20; A61B 5/7203; A61B 5/7264; A61B 5/0068; G06N 3/045
    See application file for complete search history.

(56) References Cited

U.S. PATENT DOCUMENTS

2018/0204046 A1    7/2018    Bhattacharya et al.
2018/0247107 A1    8/2018    Murthy et al.

OTHER PUBLICATIONS

"Anna M. Buchner et al., Comparison of Probe-Based Confocal Laser Endomicroscopy With Virtual Chromoendoscopy for Classifications of Colon Polyps, Mar. 2010, Gastroenterology, vol. 138, Issue 3, pp. 834-842" (Year: 2010).*

Farhad Ghazvinian et. al., "Stain Normalization of Histopathology Images using Generative Adversarial Networks, 2018, IEEE 15th International Symposium on Biomedical Image, ISBI 2018" (Year: 2018).*

International Search Report and Written Opinion for PCT/US2020/15332, dated Apr. 24, 2020 (20 pages).

Izadyyazdanabadi et al., "Weakly-Supervised Learning-Based Feature Localization for Confocal Laser Endomicroscopy Glioma Images," Medical Image Computing and Computer Assisted Intervention, MICCAI 2018, pp. 300-308 (2018).

Krizhevsky, A., et al., "ImageNet classification with deep convolutional neural networks," Advances in neural Information processing systems, pp. 1097-1105 (2012).

Simonyan et al., "Very Deep Convolutional Networks for Large-Scale Image Recognition," available from arXiv(dot)org, arXiv identifier 1409.1556 (2014).

Szegedy, C., et al., "Going deeper with convolutions," Proceedings of the IEEE conference on Computer Vision and Pattern Recognition, pp. 1-9 (2015).

Extended European Search Report for European Patent Application No. 20747730.8, dated Oct. 27, 2022 (7 pages).

Gatys et al: "Image Style 1-19 Transfer Using Convolutional Neural Networks", 2016 IEEE Conference on Computer Vision and Pattern Recognition (CVPR), Jun. 1, 2016 (Jun. 1, 2016), pp. 2414-2423, XP055571216, DOI: 10.1109/CVPR.2016.265 ISBN: 78-1-4673-8851-1.

Izadyyazdanabadi et al: "Convolutional Neural Networks: Ensemble Modeling, Fine-Tuning and Unsupervised Semantic Localization for Intraoperative CLE Images", arxiv.org, Cornell University Library, 201 Olin Library Cornell University Ithaca, NY 14853, Sep. 10, 2017 (Sep. 10, 2017), pp. 1-30, XP081294861, DOI:10.1016/J.JVCIR.2018.04.004.

Tarek et al: "StainGAN: Stain Style Transfer for Digital Histological Images", arxiv.org, Cornell University Library, 201 Olin Library Cornell University Ithaca, NY 14853, Apr. 4, 2018 (Apr. 4, 2018), pp. 1-8.

* cited by examiner

Target Image at Iteration $i$

Red Channel  Green Channel  Blue Channel

Target Image at Iteration $i + 1$

| +1 | +1 | +1 |    |    |    |
|----|----|----|----|----|----|
| +1 | +1 | +1 |    |    |    |
| +1 | +1 |    |    | +1 |    |
|    |    |    | +1 | +1 |    |
|    |    |    |    | +1 |    |
|    |    |    |    |    |    |

| -1 | -1 |    |    |    |    |
|----|----|----|----|----|----|
| -1 |    |    |    |    |    |
|    |    |    |    | -1 |    |
|    |    |    | -1 | -1 |    |
|    |    |    |    | -1 |    |
|    |    |    |    |    |    |

| +1 | +1 | +1 |    |    |    |
|----|----|----|----|----|----|
| +1 | +1 |    |    |    |    |
| +1 |    |    |    |    |    |
|    |    |    |    |    | -1 |
|    |    |    |    |    |    |
|    |    |    |    |    |    |

Red Channel  Green Channel  Blue Channel

Target Image at Iteration $i + 2$

| +2 | +2 | +1 | +1 |    |    |
|----|----|----|----|----|----|
| +2 | +1 | +1 |    |    |    |
| +1 | +1 | +1 |    |    |    |
| +1 |    |    |    |    |    |
|    |    |    |    |    |    |
|    |    |    |    |    |    |

| -2 | -2 | -1 | -1 |    |    |
|----|----|----|----|----|----|
| -2 | -1 | -1 |    |    | -1 |
| -1 | -1 |    |    | -1 | -2 |
| -1 |    |    |    | -2 | -2 |
|    |    |    |    | -1 | -2 |
|    |    |    |    |    | -1 |

| +2 | +2 | +1 | +1 |    |    |
|----|----|----|----|----|----|
| +2 | +1 | +1 |    |    |    |
| +1 | +1 |    |    |    | -1 |
|    |    |    |    | -1 | -2 |
|    |    |    |    |    | -1 |
|    |    |    |    |    |    |

Red Channel  Green Channel  Blue Channel

Critical Structures Removed During Style Transfer

Artifacts Added During Style Transfer

SYSTEMS, METHODS, AND MEDIA FOR AUTOMATICALLY TRANSFORMING A DIGITAL IMAGE INTO A SIMULATED PATHOLOGY IMAGE

CROSS REFERENCE TO RELATED APPLICATIONS

This application represents the United States national stage filing of PCT/US2020/015332, filed Jan. 28, 2020, which is based on, claims the benefit of, and claims priority to U.S. Provisional Application No. 62/797,784 filed on Jan. 28, 20182019, which is hereby incorporated herein by reference in its entirety for all purposes.

STATEMENT REGARDING FEDERALLY SPONSORED RESEARCH

N/A

BACKGROUND

Recent advances in endomicroscopic imaging technologies, such as confocal laser endomicroscopy (CLE), have led to increased use of such technologies during surgeries or other interventions to image tissue in vivo, rather than extracting tissue for examination ex vivo (e.g., using conventional light microscopy). For example, such technologies have been investigated for the potential to assist neurosurgeons in examining a dissection bed during brain surgery. Endomicroscopic imaging technologies offer many potential advantages. For example, endomicroscopic imaging technologies can facilitate in vivo scanning of tissue and/or a surgical resection bed intraoperatively, which can be used to essentially produce optical biopsies much more quickly than conventional biopsies can be prepared. As another example, some endomicroscopic imaging technologies, such as CLE, can be used with various different fluorophores allowing the technology to be used in various anatomical regions. As yet another example, such endomicroscopic imaging technologies generally utilize small probes, and the whole system is often portable. However, interpreting images generated using endomicroscopic imaging technologies can present difficulties, as the images that are produced are dramatically different than images that pathologists may be most familiar with. For example, the most frequent imaging technique used for neurosurgical intraoperative diagnosis is based on histology slides, which are commonly hematoxylin and eosin (H&E)-stained sections. Accordingly, although endomicroscopic imaging technologies can generate high quality images a pathologist or other medical provider that most often makes diagnoses based on H&E-stained sections may not be as confident in evaluating such images.

In a more particular example, handheld CLE devices can be used during neurosurgery related to the treatment of brain tumors to aid neurosurgeons in distinguishing tissue that is part of a tumor from healthy tissue. These CLE devices can provide real-time (or near real-time) cellular-scale images of histopathological features of the tissue in vivo during surgery by capturing images at a rate of about one or more per second. This can generate large numbers of images (e.g., on the order of hundreds to thousands). However, many of the images of brain tissue captured by CLE devices during brain surgery are not diagnostically useful. For example, while a wide range of fluorophores can be used for imaging using CLE devices in gastroenterology applications, fluorophore options for use in neural imaging are few, and those that are available for in vivo use in the human brain may not be as effective as fluorophores that can be used in other applications.

More particularly, some of the images captured by CLE devices while using fluorescein sodium (FNa) can include artifacts produced by motion of the probe, or by blood blocking at least a portion of the field of view of the CLE device. Images with such artifacts may not be useful in making a diagnostic determination. In addition to the potential difficulties of evaluating gray scale images produced by a CLE device (e.g., rather than an H&E-stained section), it may take significant amounts of time for the surgeon or pathologist to sort non-diagnostic frames (e.g., frames that do not include features that are useful for making a diagnostic determination, frames that include artifacts that render the frame unusable for diagnosis, etc.) from diagnostic frames (e.g., frames that include features that are useful for making a diagnostic determination, and that do not include artifacts that render the frame unusable for diagnosis, etc.) during the operation to make an intraoperative diagnosis. In some cases, if a surgeon wishes to make an intraoperative diagnosis using the images from the CLE device, the time it takes to sort through the images can increase the length of the surgery compared to an ideal case where the surgeon or pathologist making the diagnosis were presented with only diagnostically relevant images. For example, one study concluded that about half of the images acquired using a CLE device were non-diagnostic due to the abundance of motion and blood artifacts, or lack of histopathological features. FIG. 1 shows examples of non-diagnostic images captured using CLE techniques. FIG. 2 shows examples of diagnostic images captured using CLE techniques.

With the ongoing growth of medical imaging technologies, which are able to produce large numbers of images, assessment of image quality is becoming more important to take the burden off practitioners in selecting diagnostic images, and allowing the practitioners to focus on making diagnostic determinations. However, as described above, artifacts may be introduced to the images during the acquisition of the image, with some of the most common artifacts in images captured by CLE including blurring, noise and low/inhomogeneous contrast.

Artifacts can be included in CLE images for a variety of reasons. For example, blurring can occur in CLE images from a maladjusted focal plane (sometimes referred to as focal blur) or from relative motion between the probe and brain tissue under examination (sometimes referred to as motion blur). As another example, environmental noise can be introduced in the detectors. As yet another example, aliasing can cause a variety of artifacts including unwanted jagged edges, geometric distortions and inhomogeneity of contrast. While many non-useful images are distorted due to motion or blood artifacts, many other images without artifacts also lack diagnostic features immediately informative to the physician. Examining all the hundreds, or thousands, of images from a single case to discriminate diagnostic images from non-diagnostic images can be tedious and time consuming.

Even if automated techniques are used to provide assistance to a surgeon, pathologist, and/or other medical practitioner in sorting diagnostic and non-diagnostic images, images identified as being diagnostic may be difficult to interpret due to the presence of artifacts and/or the absence of features that would be most useful to a human evaluator.

Accordingly, systems, methods, and media for automatically transforming a digital image into a simulated pathology image are desirable.

SUMMARY

In accordance with some embodiments of the disclosed subject matter, systems, methods, and media for automatically transforming a digital image into a simulated pathology image are provided.

In accordance with some embodiments of the disclosed subject matter, a method for transforming a digital image generated by an endomicroscopy device into a simulated pathology image is provided, the method comprising: receiving a first image captured by the endomicroscopy device; providing the first image to a first pre-trained convolutional neural network, wherein the first pre-trained convolutional neural network was trained to recognize at least a multitude of classes of objects; receiving, from a first hidden layer of the first pre-trained convolutional neural network, a first plurality of features indicative of content of the first image; receiving a second plurality of features indicative of a style of a second image that depicts a portion of a histopathology slide; receiving a third plurality of features indicative of content of the third image; receiving a fourth plurality of features indicative of a style of the third image; generating a first loss value based on the first plurality of features, the second plurality of features, the third plurality of features, and the fourth plurality of features, wherein the first loss value is indicative of similarity between the content of the first image and the third image and similarity between the style of the second image and the style of the third image; generating a fourth image by modifying values associated with one or more pixels of the third image based on the first loss value; providing the fourth image to the first pre-trained convolutional neural network; receiving, from the first hidden layer of the first pre-trained convolutional neural network, a fifth plurality of features indicative of content of the fourth image; providing the fourth image to a second pre-trained convolutional neural network, wherein the second pre-trained convolutional neural network is trained to recognize at least the multitude of classes of objects; receiving, from a second hidden layer of the second pre-trained convolutional neural network, a sixth plurality of features indicative of a style of the fourth image; generating a second loss value based on the first plurality of features, the second plurality of features, the fifth plurality of features, and the sixth plurality of features, wherein the second first loss value is indicative of similarity between the content of the first image and the fourth image and similarity between the style of the second image and the style of the fourth image; generating a fifth image by modifying values associated with one or more pixels of the fourth image based on the second loss value; and causing the fifth image to be presented using a display.

In some embodiments, the endomicroscopy device is a confocal laser endomicroscopy device, and the first image was generated by the confocal laser endomicroscopy device during a surgical procedure, and the method further comprises: causing the fifth image to be presented during the surgical procedure for evaluation by a medical provider associated with the surgery.

In some embodiments, the first pre-trained convolutional neural network and the second pre-trained convolutional neural network have the same architecture.

In some embodiments, the first pre-trained convolutional neural network and the second pre-trained convolutional neural network have the same parameter values.

In some embodiments, the first pre-trained convolutional neural network and the second pre-trained convolutional neural network are instances of a VGG-19 convolutional neural network, wherein the multitude of classes of objects correspond to at least a portion of the classes defined by a third party that maintains a database of labeled images (e.g., the ImageNet dataset of labeled images), and wherein the first plurality of features, the fourth plurality of features, and the sixth plurality of features are generated by a first instance of the VGG-19 convolutional neural network, and the third plurality of features are generated by a second instance of the VGG-19 convolutional neural network.

In some embodiments, the VGG-19 convolutional neural network was trained using images from the dataset of labeled images.

In some embodiments, the first hidden layer is a convolutional layer.

In some embodiments, the second hidden layer is a first rectified linear unit (ReLU) layer.

In some embodiments, the method further comprises: receiving, from a second ReLU layer of the second pre-trained convolutional neural network, a seventh plurality of features indicative of a style of the second image, wherein the second ReLU layer generates a greater number of features than the first ReLU layer; and generating the first loss value based on the second plurality of features and the seventh plurality of features.

In some embodiments, the method further comprises: generating a first Gram matrix based on the second plurality of features; generating a second Gram matrix based on the seventh plurality of features; and generating the first loss value using the first Gram matrix and the second Gram matrix.

In some embodiments, the method further comprises: generating the first loss value using a first loss function, the first loss function corresponding to the following expression:

$$\text{Loss}_{Total} = \frac{1}{2} \sum (C_{Content} - C_{Target})^2 + \alpha \times \sum_{i=1}^{5} w^i \times \sum \left(S_{Ref}^i - S_{Target}^i\right)^2$$

where $C_{Content}$ corresponds to the first plurality of features, $C_{Target}$ corresponds to the third plurality of features, $S_{Ref}^i$ corresponds to features indicative of a style of the second image and includes $S_{Ref}^1$ corresponding to the second plurality of features, and $S_{target}^i$ corresponds to features indicative of a style of the third image and includes $S_{target}^1$ corresponding to the fourth plurality of features, $w^i$ corresponds to weights that control how much each of i layers of the second pre-trained convolutional neural network influence the loss value, $\alpha$ is a parameter that controls relative weights of a style portion of the loss and a content portion of the loss, and $\text{Loss}_{Total}$ corresponds to the first loss value.

In some embodiments, each of the weights $w^i$ are 0.2, and $\alpha$ is 100.

In some embodiments, the second image is an image of a hematoxylin and eosin stained tissue sample.

In some embodiments, the first image depicts tissue associated with a first subject, and the second image depicts tissue extracted from a second subject.

In some embodiments, the first image depicts brain tissue, and wherein the second image depicts a portion of a glioma tumor.

In some embodiments, the third image is identical to the first image, and the fourth image is a modified version of the first image.

In accordance with some embodiments of the disclosed subject matter, a method for transforming a digital image generated by an endomicroscopy device into a simulated pathology image is provided, the method comprising: (a) receiving a first image depicting in vivo tissue of a first subject; (b) generating a first plurality of features indicative of content of the first image using a first hidden layer of a first pre-trained convolutional neural network trained to recognize at least a multitude of classes of common objects; (c) receiving a second plurality of features indicative of style of a second image corresponding to features generated using a second hidden layer of the pre-trained convolutional neural network, wherein the second image depicts a histopathology slide prepared using tissue of a second subject; (d) generating a third image; (e) generating a third plurality of features indicative of content of the third image using the first hidden layer; (f) generating a fourth plurality of features indicative of a style of the third image using the second hidden layer; (g) generating a loss value based on a loss function using the first plurality of features, the second plurality of features, the third plurality of features, and the fourth plurality of features; (h) modifying the third image based on the loss value; (i) repeating (e) through (h) until a criterion is satisfied; and (j) causing a final version of the third image to be presented in response to the criterion being satisfied.

In some embodiments, the method further comprises: determining that a current value of the loss function is different than an immediately preceding value of the loss function by less than a particular amount; and in response to determining that a current value of the loss function is different than an immediately preceding value of the loss function by less than the particular amount, determining that the criterion is satisfied.

In some embodiments, the method further comprises: determining that (e) through (h) have been repeated a particular number of time; and in response to determining that (e) through (h) have been repeated a particular number of time, determining that the criterion is satisfied.

In accordance with some embodiments, a system is provided, the system comprising: an endomicroscopy device, comprising: a probe; and a light source, wherein the endomicroscopy device is configured to generate image data representing a subject's tissue during an interventional procedure; and a computing device comprising: a hardware processor; and memory storing computer-executable instructions that, when executed by the processor, cause the processor to: receive a first image captured by the endomicroscopy device; provide the first image to a first pre-trained convolutional neural network, wherein the first pre-trained convolutional neural network is trained to recognize at least a multitude of classes of objects; receive, from a first hidden layer of the first pre-trained convolutional neural network, a first plurality of features indicative of content of the first image; receive a second plurality of features indicative of a style of a second image that depicts a portion of a histopathology slide; receive a third plurality of features indicative of content of the third image; receive a fourth plurality of features indicative of a style of the third image; generate a first loss value based on the first plurality of features, the second plurality of features, the third plurality of features, and the fourth plurality of features, wherein the first loss value is indicative of similarity between the content of the first image and the third image and similarity between the style of the second image and the style of the third image; generate a fourth image by modifying values associated with one or more pixels of the third image based on the first loss value; provide the fourth image to the first pre-trained convolutional neural network; receive, from the first hidden layer of the first pre-trained convolutional neural network, a fifth plurality of features indicative of content of the fourth image; provide the fourth image to a second pre-trained convolutional neural network, wherein the second pre-trained convolutional neural network was trained to recognize at least the multitude of classes of objects; receive, from a second hidden layer of the second pre-trained convolutional neural network, a sixth plurality of features indicative of a style of the fourth image; generate a second loss value based on the first plurality of features, the second plurality of features, the fifth plurality of features, and the sixth plurality of features, wherein the second first loss value is indicative of similarity between the content of the first image and the fourth image and similarity between the style of the second image and the style of the fourth image; generate a fifth image by modifying values associated with one or more pixels of the fourth image based on the second loss value; and cause the fifth image to be presented using a display.

In accordance with some embodiments of the disclosed subject matter, a system is provided, the system comprising: an endomicroscopy device, comprising: a probe; and a light source, wherein the endomicroscopy device is configured to generate image data representing a subject's tissue during an interventional procedure; and a computing device comprising: a hardware processor; and memory storing computer-executable instructions that, when executed by the processor, cause the processor to: (a) receive a first image depicting in vivo tissue of a first subject; (b) generate a first plurality of features indicative of content of the first image using a first hidden layer of a first pre-trained convolutional neural network trained to recognize at least a multitude of classes of common objects; (c) receive a second plurality of features indicative of style of a second image corresponding to features generated using a second hidden layer of a the pre-trained convolutional neural network, wherein the second image depicts a histopathology slide prepared using tissue of a second subject; (d) generate a third image; (e) generate a third plurality of features indicative of content of the third image using the first hidden layer; (f) generate a fourth plurality of features indicative of a style of the third image using the second hidden layer; (g) generate a loss value based on a loss function using the first plurality of features, the second plurality of features, the third plurality of features, and the fourth plurality of features; (h) modify the third image based on the loss value; (i) repeat (e) through (h) until a criterion is satisfied; and (j) cause a final version of the third image to be presented in response to the criterion being satisfied.

In accordance with some embodiments of the disclosed subject matter, a non-transitory computer readable medium containing computer executable instructions that, when executed by a processor, cause the processor to perform a method for transforming a digital image generated by an endomicroscopy device into a simulated pathology image is provided, the method comprising: receiving a first image captured by the endomicroscopy device; providing the first image to a first pre-trained convolutional neural network, wherein the first pre-trained convolutional neural network is trained to recognize at least a multitude of classes of objects; receiving, from a first hidden layer of the first pre-trained convolutional neural network, a first plurality of features indicative of content of the first image; receiving a second plurality of features indicative of a style of a second image that depicts a portion of a histopathology slide; receiving a third plurality of features indicative of content of a third image; receiving a fourth plurality of features indicative of a style of the third image; generating a first loss value based on the first plurality of features, the second plurality of features, the third plurality of features, and the fourth plurality of features, wherein the first loss value is indicative of similarity between the content of the first image and the third image and similarity between the style of the second image and the style of the third image; generating a fourth image by modifying values associated with one or more pixels of the third image based on the first loss value; providing the fourth image to the first pre-trained convolutional neural network; receiving, from the first hidden layer of the first pre-trained convolutional neural network, a fifth plurality of features indicative of content of the fourth image; providing the fourth image to a second pre-trained convolutional neural network, wherein the second pre-trained convolutional neural network is trained to recognize at least the multitude of classes of objects; receiving, from a second hidden layer of the second pre-trained convolutional neural network, a sixth plurality of features indicative of a style of the fourth image; generating a second loss value based on the first plurality of features, the second plurality of features, the fifth plurality of features, and the sixth plurality of features, wherein the second first loss value is indicative of similarity between the content of the first image and the fourth image and similarity between the style of the second image and the style of the fourth image; generating a fifth image by modifying values associated with one or more pixels of the fourth image based on the second loss value; and causing the fifth image to be presented using a display.

In accordance with some embodiments of the disclosed subject matter, a non-transitory computer readable medium containing computer executable instructions that, when executed by a processor, cause the processor to perform a method for transforming a digital image generated by an endomicroscopy device into a simulated pathology image is provided, the method comprising: (a) receiving a first image depicting in vivo tissue of a first subject; (b) generating a first plurality of features indicative of content of the first image using a first hidden layer of a pre-trained convolutional neural network trained to recognize at least a multitude of classes of common objects; (c) receiving a second plurality of features indicative of style of a second image corresponding to features generated using a second hidden layer of the pre-trained convolutional neural network, wherein the second image depicts a histopathology slide prepared using tissue of a second subject; (d) generating a third image; (e) generating a third plurality of features indicative of content of the third image using the first hidden layer; (f) generating a fourth plurality of features indicative of a style of the third image using the second hidden layer; (g) generating a loss value based on a loss function using the first plurality of features, the second plurality of features, the third plurality of features, and the fourth plurality of features; (h) modifying the third image based on the loss value; (i) repeating (e) through (h) until a criterion is satisfied; and (j) causing a final version of the third image to be presented in response to the criterion being satisfied.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with some embodiments of the disclosed subject matter, systems, methods, and media for automatically transforming a digital image into a simulated pathology image are provided.

In some embodiments, the mechanisms described herein can receive a digital image generated from an endomicroscopy device, and can automatically transform the received image to a version that simulates an image of an tissue sample prepared using conventional techniques and captured using conventional light microscopy (or viewed via optics of a conventional microscope). For example, the mechanisms described herein can generate a version of the digital image that simulates an H&E stained tissue sample.

Figure 1:
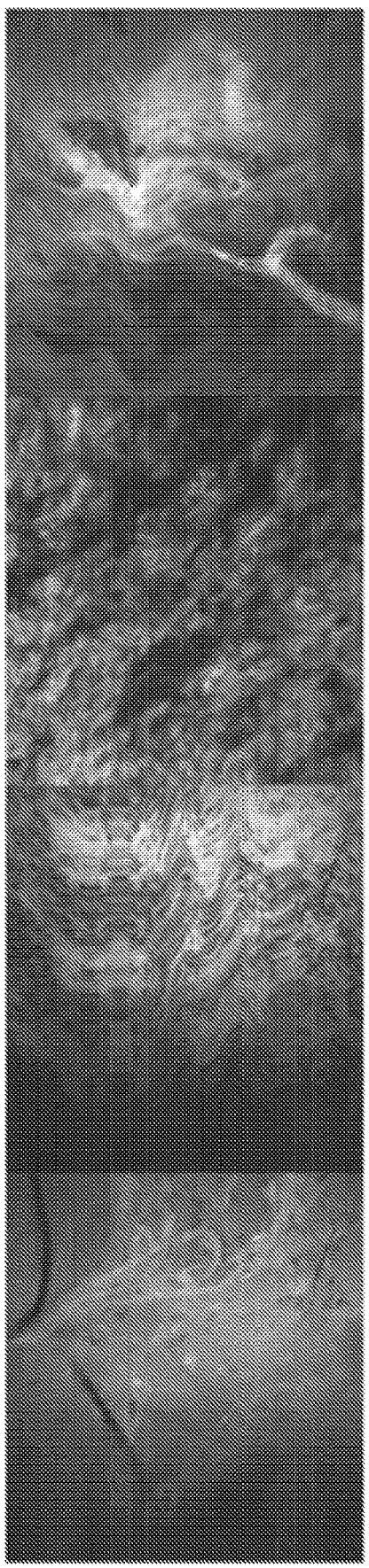
FIG. 1 shows examples of non-diagnostic images captured using CLE techniques.
Figure 1:
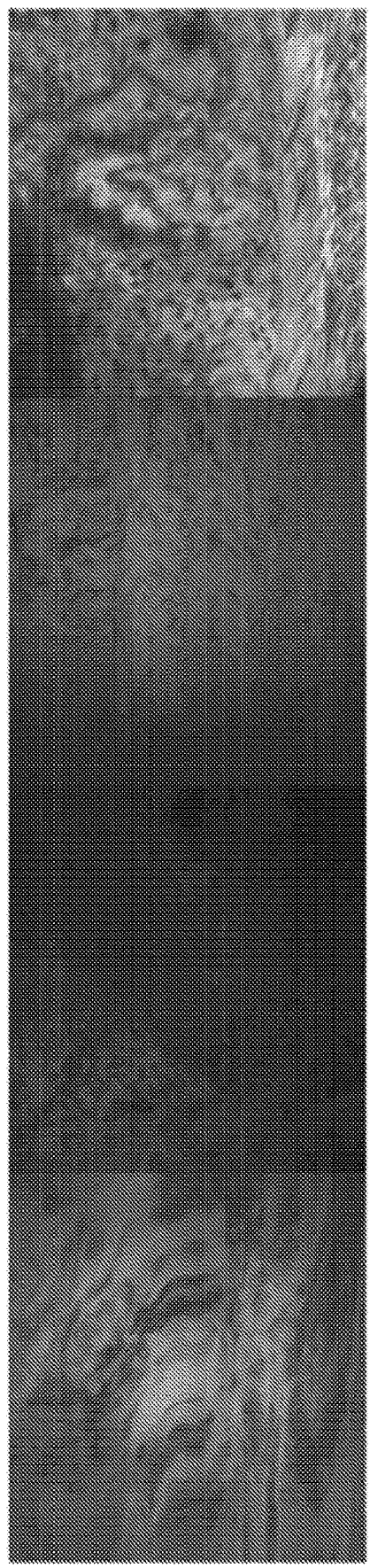
Figure 2:
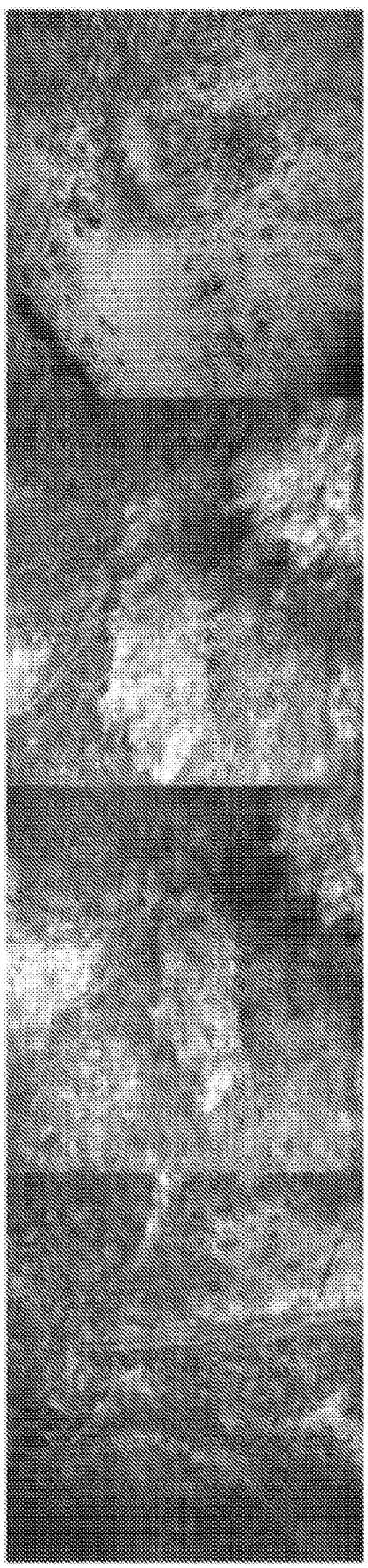
FIG. 2 shows examples of diagnostic images captured using CLE techniques.
Figure 2:
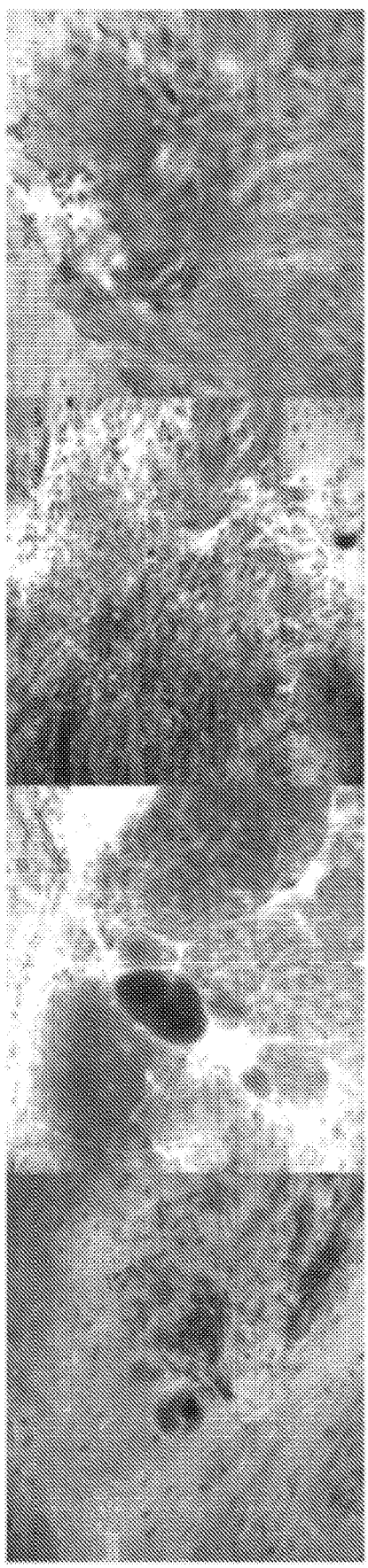
Figure 3:
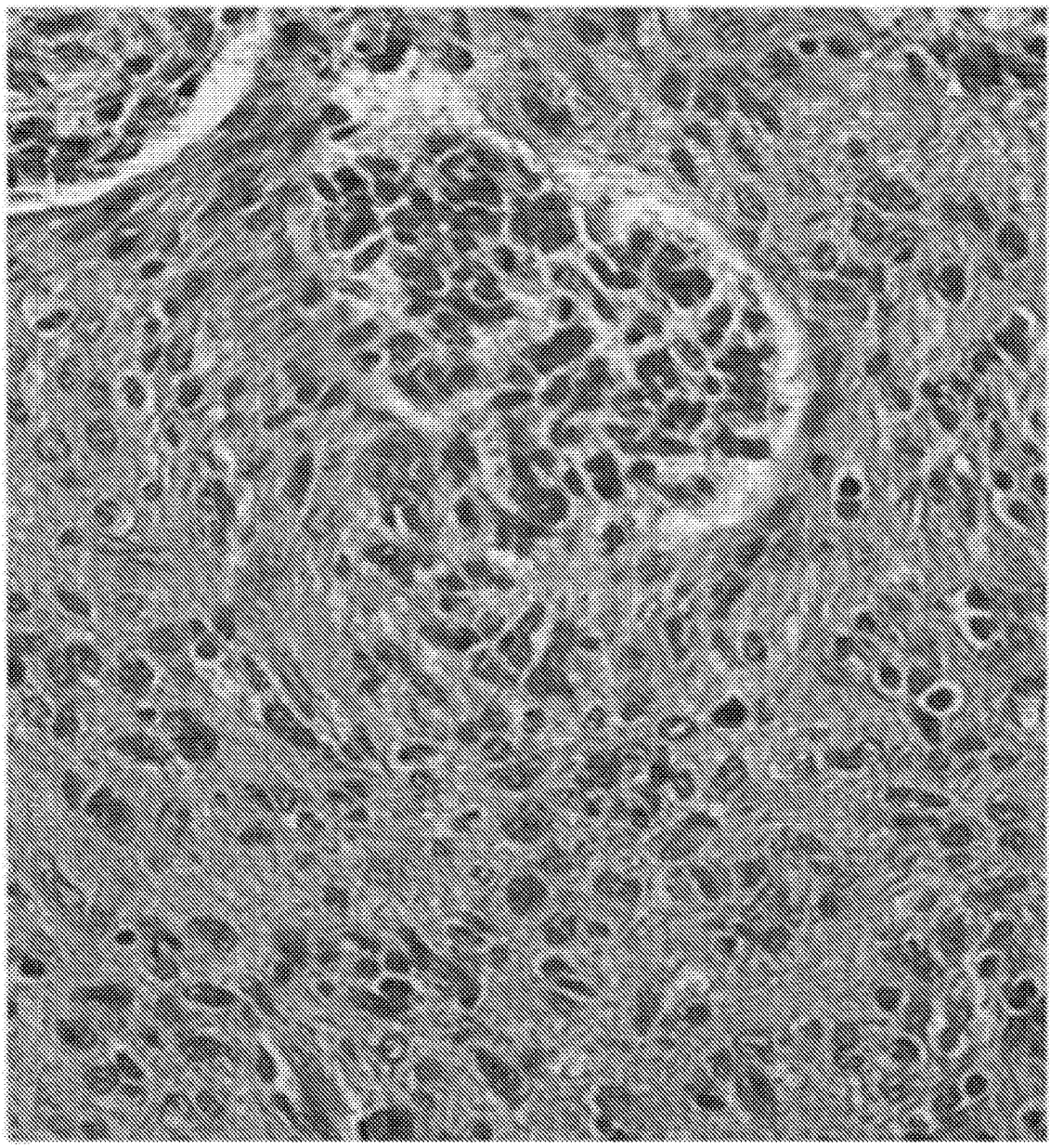
FIG. 3 shows an example of a tissue sample from a glioma tumor that has been fixed and stained using hematoxylin and eosin stain and acquired using conventional light microscopy that can be used as a style reference image in some embodiments of the disclosed subject matter.

FIG. 3 shows an example of a tissue sample from a glioma tumor that has been fixed and stained using H&E stain and acquired using conventional light microscopy that can be used as a style reference image in some embodiments of the disclosed subject matter. More particularly, FIG. 3 shows an example of an image depicting a formalin fixed H&E stained section that can be used as a style reference image. In some embodiments, the mechanisms described herein can receive an image generated using a CLE device, and can use a micrograph of a tissue sample prepared in the style which is to be used as a style template. For example, the mechanisms described herein can receive one or more of the images shown in FIG. 2, and can use the image in FIG. 3 in a process to transform the received image into an H&E style image. The image in FIG. 3 captured using conventional light microscopy techniques can on the order of tens of minutes to hours to create. In general, H&E stained tissue samples can be created using different procedures. For example, H&E stained tissue samples can be created using a frozen section procedure in which a sample can be rapidly frozen to −20 to −30° C., and sliced using a microtome. A slice can then be stained using H&E to create an H&E stained tissue sample relatively quickly. A frozen section procedure can potentially create a slide suitable for analysis within about 20 minutes from when the tissue is excised, but can take significantly longer in some cases. As another example, H&E stained tissue samples can be created using a formalin-fixed paraffin-embedded (FFPE) procedure, in which excised tissue can be fixed with formalin (also known as formaldehyde) and embedding the fixed tissue in a paraffin wax block. Once the tissue is embedded in the wax block it can be sliced to create thin sections, which can then be stained (e.g., using H&E). Generating slides using FFPE procedure can be significantly more time consuming than frozen section procedures, but also typically produces higher quality slides.

In some embodiments, the mechanisms described herein can receive images from an endomicroscopic imaging device (e.g., a CLE device) at a rate of up to one or more per second. This can facilitate much faster and less invasive review of tissue samples than is possible with conventional frozen section or FFPE procedures. However, although such devices can generate images of tissue at a similar scale much more quickly, many such images may be non-optimal due to the presence of artifacts such as background noise, blur, and red blood cells. Additionally, histopathological features that can be used to determine whether a tissue sample being imaged is normal tissue or abnormal tissue are typically more easily identified in H&E slides (or other conventional slide preparation techniques) compared to the images generated using an endomicroscopic device. For example, CLE images of brain tissue may be generated using nonspecific fluorescent dyes such as fluorescein sodium (FNa), as many other fluorophores are not suitable for use within the brain. In general, histopathological features of structures within the brain, such as features of glioma tumors, are more easily identified from images of H&E slides of excised tissue. Additionally, medical practitioners, such as neuropathologists, are often more comfortable analyzing tissue samples stained with H&E for neurological diagnoses, especially for frozen section biopsies. However, fluorescent images from intraoperative neurosurgical application present a new digital imaging environment to the neuropathologist for diagnosis that may include hundreds of images from one case in a form that the neuropathologist is less familiar with. For example, the U.S. FDA has recently approved a blue laser range CLE system primarily utilizing FNa for use in neurosurgery.

In some embodiments, the mechanisms described herein can improve some images generated using endomicroscopy technologies (e.g., CLE technologies) to make the images more suitable for analysis by a medical practitioner by transforming the images in various ways. For example, the mechanisms described herein can be used to remove occluding artifacts from the images generated using endomicroscopy technologies. As another example, the mechanisms described herein can be used to make histological patterns that are difficult to recognize in the endomicroscopy images more easily discernable by a medical practitioner. Additionally, in some embodiments, the mechanisms described herein can remove occluding artifacts, and amplify histological patterns in the image without removing critical details (e.g., cells) or generating entirely new patterns that are not actually present in the tissue. In some embodiments, the mechanisms described herein can generate and present "transformed" CLE images to a neuropathologist and/or a neurosurgeon that may resemble images in a familiar and standard appearance from histology stains, such as H&E.

If a suitable dataset of endomicroscopic images and colocalized images of H&E slides of the same tissue were available, supervised learning techniques can be used to train a model to transform the endomicroscopic images into another style of image. However, this may require the images to show the same exact tissue using the two different modalities, which is infeasible because endomicroscopic images are generally generated from an in vivo sample, and capturing images of excised tissue would be unlikely to produce images with the same characteristics. For example, capturing images using a CLE device intraoperatively will generally generate artifacts (e.g., due to movements, the presence of blood, etc.) that are not generated when creating stained slides of excised tissue. As another example, creating stained slides of excised tissue can generate artifacts that are not present in images generated by a CLE device. Accordingly, although supervised learning may be capable of generating a model that maps between two imaging domains (e.g., CLE and H&E), the difficulty of creating a suitable dataset makes such an approach infeasible.

In some embodiments, the mechanisms described herein can use image style transfer techniques to transform an image generated using a particular imaging modality (e.g., CLE) to appear similar in style to an image of similar but different tissue prepared generated using a different modality (e.g., conventional light microscopy of an H&E stained tissue sample). In such embodiments, the image used as a style exemplar may be an image of similar tissue (e.g., a tissue sample excised from a glioma) that is from a different area or from a different subject entirely. In some embodiments, the mechanisms described herein can use one or more image style transform techniques to blend the content and style of two images to produce a target image (sometimes referred to as an output image, a resultant image, a resulting image, or a stylized image). In some embodiments, the techniques described herein can attempt to minimize the distance between feature maps representing the source images (e.g., a CLE image, and an image of an H&E stained tissue sample) and feature maps representing the target image. In some embodiments, feature maps can be extracted using any suitable technique or combination of techniques. For example, in some embodiments, a pretrained convolutional neural network (CNN) can be used to generate feature maps representing each of the images.

In some embodiments, the mechanisms described herein can be used to transform a digital image captured using endomicroscopy techniques to remove the occlusions that may be present and/or to enhance the appearance of structures that were difficult to perceive in the original digital images. For example, CLE images generated using non-specific FNa application during glioma surgery can be transformed to appear like in the same style as an H&E-stained histology.

In some embodiments, image style transfer techniques can use content from one image (e.g., a CLE image) and stylistic characteristics from another image as inputs, and can output a target image that is based on content from the first image (e.g., structures) with stylistic elements added such that the target image has a similar general appearance as the style image. In some embodiments, the mechanisms described herein can use a pretrained CNN that extracts feature maps from source images (e.g., content and style images) and target images. In some embodiments, the mechanisms described herein can calculate a quantitative representation of the content and style representations for the source and target images. In some embodiments, the mechanisms described herein can use a loss function to represent differences between the content representation and style representation of source images and the content and style representations of target images. In some embodiments, the mechanisms described herein can attempt to minimize the loss function using one or more optimization techniques. Note that, in contrast to CNN supervised learning, where the model parameter values are altered in an attempt to minimize the prediction error, image style transfer can be used to iteratively modify the pixel values of the target image in an attempt to minimize the loss function with the model parameters being fixed (which can result in content and style representations being stable for the content image and the style image, respectively).

In some embodiments, using a tissue sample that has been prepared using an FFPE procedure (sometimes referred to as a permanent histology H&E sample) can provide an intraoperative advantage in both speed and quality compared to frozen section histology. For example, an initial pathology diagnosis for brain tumor surgery is often based on frozen section histology, and a formal diagnosis is not made until permanent histology slides are analyzed, which can requiring one to several days to prepare. Frozen section histology often introduces freezing artifacts, artifacts caused by difficulties that may arise while sectioning (i.e., cutting) the sample), and may be affected by inconsistent staining for histological characteristics that are important for diagnosis. By contrast, using style transfer mechanisms described herein that are based on a permanent histology H&E sample of similar tissue can facilitate real-time analysis of rapidly acquired, on-the-fly (i.e., real time) in vivo intraoperative images (e.g., generated using a endomicroscopy techniques, such as CLE) that more closely resemble permanent histology (e.g., rather than frozen section histology), which can provide an advantage for interpretation compared to other intraoperative diagnosis techniques. In some embodiments, using techniques described herein, endomicroscopy techniques can be more comparable to permanent histology, and in some cases may be capable of capturing features that are destroyed when a sample is extracted and subjected to an FFPE procedure. For example, because CLE can be used to image live tissue in vivo, additional features may be evident (e.g., features that are transient), and artifacts caused by architectural disturbance may be avoided.

Figure 4:
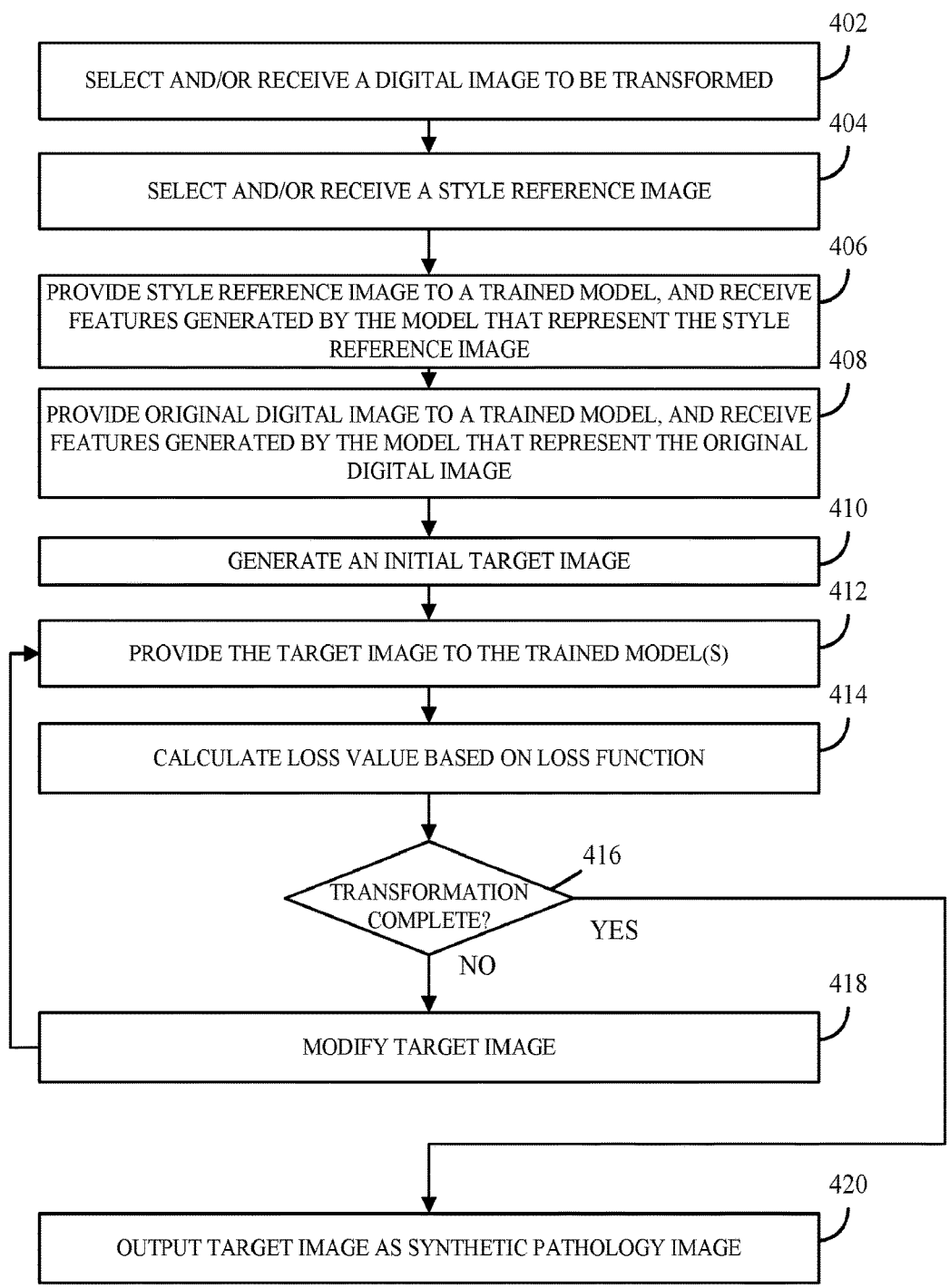
FIG. 4 shows an example of a process for automatically transforming a digital image into a simulated pathology image in accordance with some embodiments of the disclosed subject matter.

FIG. 4 shows an example 400 of a process for automatically transforming a digital image into a simulated pathology image in accordance with some embodiments of the disclosed subject matter. At 402, process 400 can select and/or receive a digital image to be transformed. In some embodiments, the digital image can be received from any suitable source, and/or can be a digital image that was generated using one or more techniques. For example, the digital image can be received from a non-volatile computer readable medium, such as memory or storage (e.g., a hard drive, flash memory, random access memory (RAM), etc.). As another example, the digital image can be received over a network (e.g., a local area network, a cellular network, a peer to peer network, etc.). As yet another example, the digital image can be received from a device that generated the digital image, such as a CLE device.

In some embodiments, process 400 can select the digital image using any suitable technique or combination of techniques. For example, in some embodiments, the digital image can be selected using a classification model configured to classify images from an endomicroscopy device based on whether the image is likely to be diagnostically useful. As another example, in some embodiments, the digital image can be selected using a classification model configured to classify images from an endomicroscopy device based on whether the image includes a particular type of tissue (e.g., normal tissue, a particular type of abnormal tissue such as a tumor). As yet another example, the digital image can be explicitly selected by a user (e.g., via a user interface). In such an example, the user interface may allow a user to select an arbitrary image from a set of images generated by the endomicroscopy device. In a more particular example, a set of images can be automatically selected for presentation via the user interface (e.g., based on an output of a classification model), and a user can select a particular image from the set of images. As still another example, each image generated by the endomicroscopy device can be selected. In some embodiments, the digital image to be transformed can be any suitable size. For example, the digital image to be transformed can be a 1024×1024 pixel image. As another example, the digital image to be transformed can be a 512×512 pixel image. As yet another example, the digital image to be transformed can be a 256×256 pixel image.

At 404, process 400 can select and/or receive a style reference image. In some embodiments, the style reference image can be an image depicting a tissue sample from a similar anatomical structure to the sample depicted in the image. For example, the style reference image can be an image of a histopathology slide prepared from a tissue sample extracted from a similar anatomical structure. In a more particular example, the style reference image can be an H&E stained slide of a tissue sample from a glioma tumor. In some embodiments, the style reference image can be any suitable size. For example, the style reference image can be a 1024×1024 pixel image. As another example, the style reference image can be a 512×512 pixel image. As yet another example, the style reference image can be a 256×256 pixel image.

In some embodiments, process 400 can select the style reference image using any suitable technique or combination of techniques. For example, a user can indicate (e.g., via a user interface) a type of tissue depicted in the digital images generated by the endomicroscopy device. As another example, a user can select (e.g., via a user interface) a style reference image to be used by process 400. As yet another example, a digital image of the tissue being imaged by the endomicroscopy device (e.g., the digital image selected and/or received at 402) can be provided to a classification model that can classify the digital image as corresponding to a particular type of tissue (e.g., normal, abnormal, a particular type of abnormal tissue such as a particular classification of tumor) and/or corresponding to a particular anatomical region (e.g., muscle tissue, brain tissue, a particular region of the brain, a particular organ, etc.). In such an example, process 400 can receive an output of the classification model and can select a style reference image corresponding to the tissue identified by the classification model. In some embodiments, process 400 can select multiple style reference images, and each can be used to generate a target image. For example, in cases in which it is unclear what type of tissue is in the digital images being generated by the endomicroscopy device.

At 406, process 400 can provide the style reference image (or images) to a trained model, and can receive style features generated by the model that represent characteristics of the image. Such style features can represent characteristics that correspond to a look of the style reference image. In some embodiments, the trained model can be a classification model that has been pretrained to recognize general objects (e.g., based on the ImageNet database), such as a convolutional neural network (CNN).

For example, in some embodiments, the trained model can be a CNN model based on the VGG-19 CNN described in Simonyan et al., "Very Deep Convolutional Networks for Large-Scale Image Recognition," available from arXiv(dot)org, arXiv identifier 1409.1556 (2014). As another example, the trained model can be a CNN model based on the VGG-16 CNN described in Simonyan. As yet another example, the trained model can be a CNN model based on the AlexNet CNN described in Krizhevsky, A., et al., "ImageNet classification with deep convolutional neural networks," *Advances in neural information processing systems*, pp. 1097-1105 (2012) ("AlexNet").

In some embodiments, the style features can be extracted from one or more hidden layers of the trained model. For example, the style features can be extracted from one or more convolution layers. As another example, the style features can be extracted from one or more rectified linear unit (ReLU) layers. As yet another example, the style features can be extracted from one or more pooling layers.

In some embodiments, the style features can be extracted from different ReLU layers of a VGG-19 CNN. For example, matrices representing the outputs of ReLU 1_1, ReLU 2_1, ReLU 3_1, ReLU 4_1, and ReLU 5_1 can be extracted. The information in the matrices can be used to generate the style features. For example, a Gram matrix can be calculated for each of the ReLU layer output matrices, and the Gram matrices can be used as style feature vectors. In such an example, using the Gram matrices of the ReLU layers can provide a representation of the style reference image that is not as dependent on the location of particular features within the image as the outputs of the ReLU layers themselves.

In some embodiments, process 400 can select a particular trained model to be used to extract features from the style reference image. For example, certain trained models may be more suitable for representing different types of tissue.

In some embodiments, process 400 can provide a particular style reference image to the trained model to generate style features once, and store the style features for later use (e.g., for calculating a loss value).

At 408, process 400 can provide an original digital image (e.g., the digital image selected at 402) to a trained model, and can receive content features generated by the model that represent characteristics of the image. In some embodiments, the trained model can be a classification model that has been pretrained to recognize general objects (e.g., based on the ImageNet database), such as a CNN.

In some embodiments, the trained model can be the same model that was used to generate the style features based on the style reference image. In such embodiments, the content features can be generated by a different portion of the model. Alternatively, in some embodiments, the trained model that is used to generate the content features can be a different trained model.

For example, in some embodiments, the trained model can be a CNN model based on the VGG-19 CNN described in Simonyan et al., "Very Deep Convolutional Networks for Large-Scale Image Recognition," available from arXiv(dot)org, arXiv identifier 1409.1556 (2014). As another example, the trained model can be a CNN model based on the VGG-16 CNN described in Simonyan. As yet another example, the trained model can be a CNN model based on the AlexNet CNN described in Krizhevsky, A., et al., "ImageNet classification with deep convolutional neural networks," *Advances in neural information processing systems*, pp. 1097-1105 (2012) ("AlexNet"). As still another example, the trained model can be a CNN model based on AlexNet ("AlexNet II"). As a further example, the trained model can be a CNN model based on the GoogLeNet CNN described in Szegedy, C., et al., "Going deeper with convolutions," *Proceedings of the IEEE conference on Computer Vision and Pattern Recognition*, pp. 1-9 (2015) ("GoogLeNet"). As another further example, the trained model can be a CNN model based on GoogLeNet ("GoogLeNet II"). Each of the preceding publications is hereby incorporated by reference herein in its entirety.

In some embodiments, the content features can be extracted from one or more hidden layers of the trained model. For example, the content features can be extracted from one or more convolution layers. As another example, the content features can be extracted from one or more ReLU layers. As yet another example, the content features can be extracted from one or more pooling layers.

In some embodiments, the style features can be extracted from a particular convolution layer of a VGG-19 CNN. For example, the content features can be a feature map output by the Conv2_1 layer, the Conv2_2 layer, the Conv3_1 layer, the Conv3_2 layer, the Conv3_3 layer, the Conv4_1 layer, the Conv4_2 layer, the Conv4_3 layer, the Conv4_4 layer, the Conv5_1 layer, the Conv5_2 layer, the Conv5_3 layer, the Conv5_4 layer, the Conv5_5 layer, any other suitable hidden layer, or a combination thereof. In some embodiments, deeper hidden layers can represent the content of the digital image more abstractly.

In some embodiments, process 400 can provide the digital image to the trained model to generate content features once, and store the content features for later use (e.g., for calculating a loss value).

At 410, process 400 can generate an initial target image. In some embodiments, the initial target image can be any suitable image with any suitable properties. For example, the initial target image can be generated by assigning random values to each pixel. As another example, the initial target image can be the digital image that was used to generate content features at 408. In some embodiments, the target image can be any suitable size. For example, the target image can be a 1024×1024 pixel image. As another example, the target image can be a 512×512 pixel image. As yet another example, the target image can be a 256×256 pixel image.

At 412, process 400 can provide the target image to the trained model (or models) used to generate the style features for the style reference image and the content features for the digital image that is to be transformed. In some embodiments, process 400 can generate style features and content features for the target image based on features extracted from the trained morel(s).

At 414, process 400 can calculate a loss value based on a loss function. Process 400 can use any suitable loss function that is configured to generate stylistically similar images while maintaining critical features of the content of the original image. In some embodiments, the following loss function can be used:

$$\text{Loss}_{Total} = \underbrace{\frac{1}{2}\sum(C_{Content} - C_{Target})^2}_{\substack{\text{Content Loss: difference} \\ \text{between content representation} \\ \text{of the content ditial image and target image}}} + \underbrace{\alpha \times \sum_{i=1}^{5} w^i \times \sum(S_{Ref}^i - S_{Target}^i)^2}_{\substack{\text{Style Loss: difference} \\ \text{between style representation} \\ \text{of the style reference image and target image}}}$$

where $C_{content}$ and $C_{Target}$ are the content representations of the digital image to be transformed and target image, $S_{Ref}^i$ and $S_{Target}^i$ are the style representations of the style reference image and target image based on the feature maps of the $i^{th}$ layer, and $w^i$ (weight of $i^{th}$ layer in the style representation) are weights that can be used to adjust which layers influence the loss function most. In one example, weights we can each be equal to 0.2. The parameter a can be adjusted to determine the relative weight of style loss in the total loss. In one example, $\alpha$ can be set to 100. The content loss and the style loss can each be summed across all elements of the feature planes, and gram matrices, respectively. For example, if content features are represented using a 128×128 matrix, the content loss can be summed across each element in a 128×128 element matrix that represents differences in the content of the digital image to be transformed and the current iteration of the target image. In such an example, the content loss at each element of the feature matrix can be calculated by subtracting the feature matrix representing the target image from the feature matrix representing the digital image to be transformed. The resulting matrix can then be squared (i.e., multiplied with itself), and the elements of the squared content loss matrix can be summed across each element to generate a content loss value. Similarly, a style loss value can be generated by subtracting gram matrices representing the style of the current iteration of the target image from gram matrices representing the style of the style reference image.

At 416, process 400 can determine whether a transformation of the digital image is complete using any suitable technique or combination of techniques. For example, process 400 can determine that the transformation of the digital image is complete after a particular number of iterations of the target image have been generated (e.g., 800, 1000, 1,600, etc.). As another example, process 400 can determine that the transformation of the digital image is complete when the loss value is below a threshold.

If process 400 determines that the transformation of the digital image is not complete ("NO" at 416), process 400 can move to 418. At 418, process 400 can modify the target image using any suitable technique or combination of techniques. In some embodiments, a limited memory optimization algorithm (e.g., a limited memory Broyden-Fletcher-Goldfarb-Shanno-based algorithm, such as L-BFGS (8)) is used at each iteration to minimize the loss value. For example, at each iteration of the target image, the optimization algorithm can be used to determine which pixel values to change, and by how much to change each pixel value in order to decrease the loss value associated with the next iteration of the target image. More generally, in some embodiments, given a target image $\text{Target}_i$ after iteration i, an optimization algorithm can be used to change the value of one or more pixels such that $\text{Loss}_{Total}$ at iteration i+1 is smaller than the value of $\text{Loss}_{Total}$ at iteration i. Additionally, in some embodiments, the optimization algorithm can be used to determine, in a limited amount of time, using a limited amount of memory and other computing resources, which combination of changes in pixel values results in $\text{Loss}_{Total}$ at iteration i+1 is smaller than the value of $\text{Loss}_{Total}$ at iteration i by a maximum amount (i.e., the optimization algorithm can be used to minimize the loss value at each iteration, given limited resources).

After modifying the target image, process 400 can return to 412 to generate content features and style features for the modified target image.

Otherwise, if process 400 determines that the transformation of the digital image is complete ("YES" at 416), process 400 can move to 420. At 420, process 400 can output the target image for evaluation. For example, process 400 can cause the target image to be presented to a medical provider, such as a surgeon, a pathologist, etc. In some embodiments, the target image can be presented using a user interface that can be configured to present both the original version of the image and the target image that has been transformed. In some embodiments, process 400 can be performed in parallel using multiple different parameters (e.g., different style images, different optimization algorithms, different pretrained CNNs, any other suitable differences in parameters, or any suitable combination thereof). In such embodiments, multiple transformations of an original digital image performed based on the different parameters, and the transformed image with the lowest final loss value can be presented to a user (e.g., a surgeon, a pathologist, etc.). Additionally or alternatively, in some embodiments, each of the multiple transformed images can be presented to a user, and the user can determine which to use in an evaluation.

Figure 5:
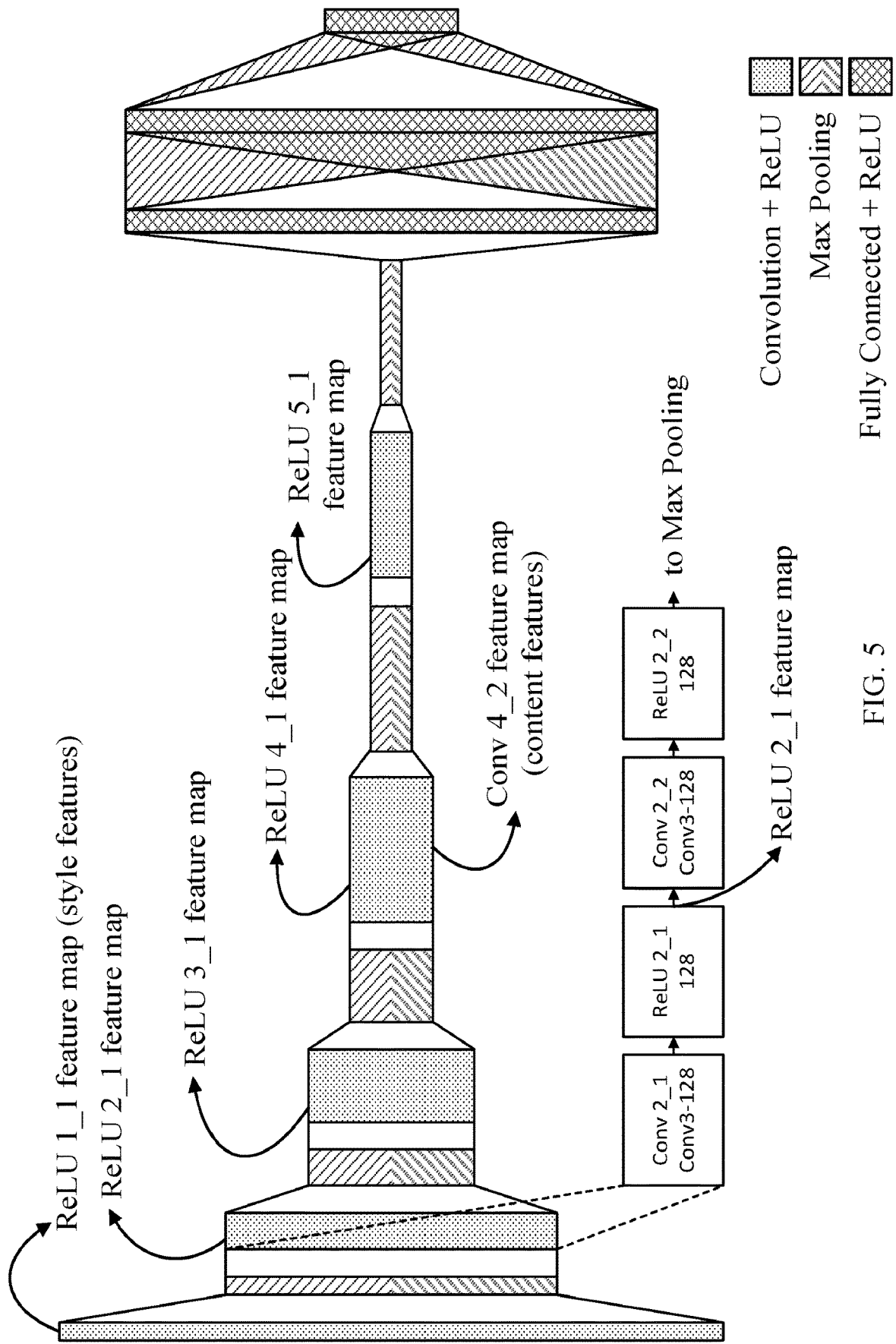
FIG. 5 shows an example of a convolutional neural network that can be pre-trained for image classification and used to generate style and/or content features that can be used in connection with a process for automatically transforming a digital image into a simulated pathology image in accordance with some embodiments of the disclosed subject matter.

In some embodiments, in addition to, or in lieu of, transforming the digital image into the target image, an image generated by an endomicroscopy device can be automatically analyzed to identify features of the image that may be diagnostically useful. Techniques that can be used to automatically identify diagnostic features of a grayscale CLE image of glioma tumors are described in Izadyyazdanabadi et al., "Weakly-Supervised Learning-Based Feature Localization for Confocal Laser Endomicroscopy Glioma Images," Medical Image Computing and Computer Assisted Intervention, MICCAI 2018, pp. 300-308 (2018), which is hereby incorporated by reference herein in its entirety. However, the techniques described in Izadyyazdanabadi et al. can be trained to automatically identify features in other types of images and/or other types of tissue. In some embodiments, the original image can be analyzed using techniques described in Izadyyazdanabadi et al., and results of the analysis can be used to identify and/or label portions of the final target image that may be diagnostically useful. FIG. 5 shows an example of a convolutional neural network that can be pre-trained for image classification and used to generate style and/or content features that can be used in connection with a process for automatically transforming a digital image into a simulated pathology image in accordance with some embodiments of the disclosed subject matter. More particularly, FIG. 5 shows an example representation of a 19-layer visual geometry group network (VGG-19), that can be pretrained on the ImageNet dataset. Features representing the style of a style reference image and a target image can be extracted from a ReLU layer of each group of layers of a particular size. Features representing the content of an original image that is to be transformed and a target image can be extracted from a particular convolutional layer.

Figure 6:
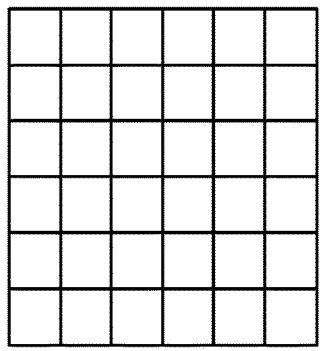
FIG. 6 shows an example of how a target image's color channels can change as the loss function is updated in accordance with some embodiments.
Figure 6:
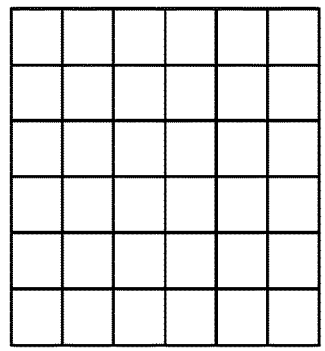
Figure 6:
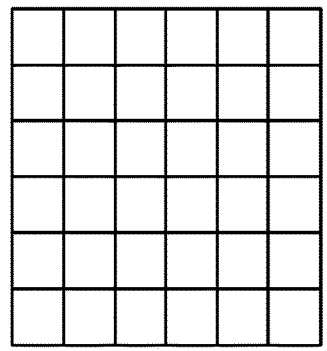

FIG. 6 shows an example of how a target image's color channels can change as the loss function is updated in accordance with some embodiments.

Figure 7:
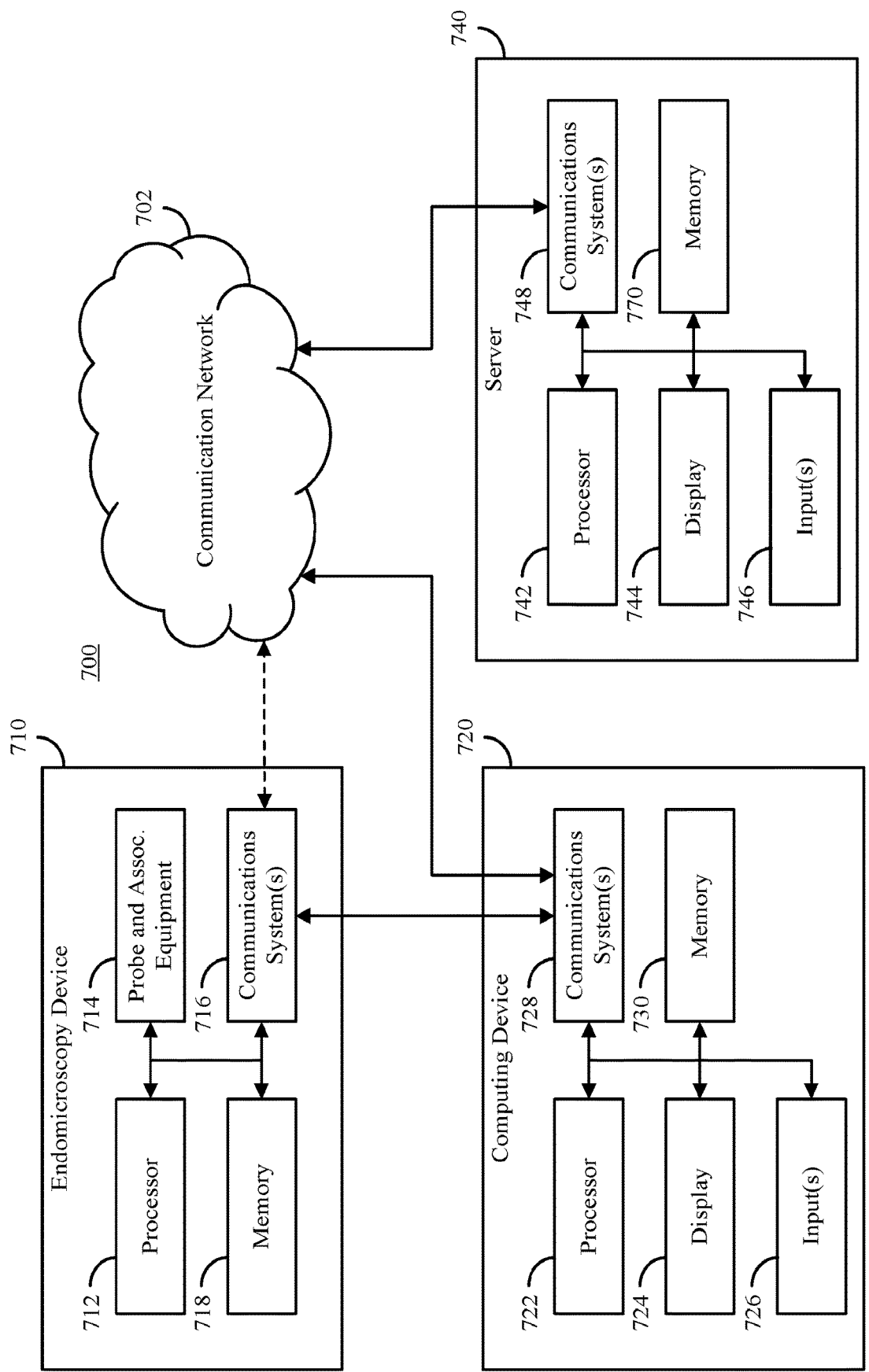
FIG. 7 shows an example of hardware that can be used to implement an endomicroscopy device (e.g., a confocal laser endomicroscopy device), a computing device, and a server in accordance with some embodiments of the disclosed subject matter.

FIG. 7 shows an example 700 of hardware that can be used to implement an endomicroscopy device 710 (e.g., a confocal laser endomicroscopy device), a computing device 720, and a server 740 in accordance with some embodiments of the disclosed subject matter. As shown in FIG. 7, in some embodiments, endomicroscopy device 710 can include a processor 712, a probe and associated equipment (e.g., a laser, a fiber optic cable, etc.) 714, one or more communication systems 716, and/or memory 718. In some embodiments, processor 712 can be any suitable hardware processor or combination of processors, such as a central processing unit (CPU), a graphics processing unit (GPU), etc. In some embodiments, communications system(s) 716 can include any suitable hardware, firmware, and/or software for communicating information to computing device 720, over communication network 702 and/or any over other suitable communication networks. For example, communications systems 716 can include one or more transceivers, one or more communication chips and/or chip sets, etc. In a more particular example, communications systems 726 can include hardware, firmware and/or software that can be used to communicate data over a coaxial cable, a fiber optic cable, an Ethernet connection, a USB connection, to establish a Wi-Fi connection, a Bluetooth connection, a cellular connection, etc.

In some embodiments, memory 718 can include any suitable storage device or devices that can be used to store instructions, values, etc., that can be used, for example, by processor 712 to control operation of probe 714, to communicate with computing device 720 and/or server 740 via communications system(s) 716, etc. Memory 718 can include any suitable volatile memory, non-volatile memory, storage, or any suitable combination thereof. For example, memory 718 can include RAM, ROM, EEPROM, one or more flash drives, one or more hard disks, one or more solid state drives, one or more optical drives, etc. In some embodiments, memory 718 can have encoded thereon a computer program for controlling operation of endomicroscopy device 710. In such embodiments, processor 712 can execute at least a portion of the computer program to capture images of tissue via probe 714.

In some embodiments, computing device 720 can include a processor 722, a display 724, one or more inputs 726, one or more communication systems 728, and/or memory 730. In some embodiments, processor 722 can be any suitable hardware processor or combination of processors, such as a CPU, a GPU, etc. In some embodiments, display 724 can include any suitable display devices, such as a computer monitor, a touchscreen, a television, etc. In some embodiments, inputs 726 can include any suitable input devices and/or sensors that can be used to receive user input, such as a keyboard, a mouse, a touchscreen, a microphone, etc.

In some embodiments, communications systems 728 can include any suitable hardware, firmware, and/or software for communicating with endomicroscopy device 710, for communicating information over communication network 702 (e.g., to and/or from server 740), and/or for communicating over any other suitable communication networks. For example, communications systems 728 can include one or more transceivers, one or more communication chips and/or chip sets, etc. In a more particular example, communications systems 728 can include hardware, firmware and/or software that can be used to establish a coaxial connection, a fiber optic connection, an Ethernet connection, a USB connection, a Wi-Fi connection, a Bluetooth connection, a cellular connection, etc.

In some embodiments, memory 730 can include any suitable storage device or devices that can be used to store instructions, values, etc., that can be used, for example, by processor 722 to present content using display 724, to communicate with one or more endomicroscopy devices 710, to communicate with server 740, etc. Memory 730 can include any suitable volatile memory, non-volatile memory, storage, or any suitable combination thereof. For example, memory 730 can include RAM, ROM, EEPROM, one or more flash drives, one or more hard disks, one or more solid state drives, one or more optical drives, etc. In some embodiments, memory 730 can have encoded thereon a computer program for controlling operation of computing device 720. In such embodiments, processor 722 can execute at least a portion of the computer program to receive one or more digital images, extract content and/or style features from the digital images, generate and modify a target image, present the a target image to a user via a user interface, receive input from a user via a user interface, etc. For example, processor 722 can execute one or more portions of process 400. In some embodiments, computing device 720 can be any suitable computing device, such as a personal computer, a laptop computer, a tablet computer, a smartphone, a server, a wearable computer, etc.

In some embodiments, server 740 can include a processor 742, a display 744, one or more inputs 746, one or more communication systems 748, and/or memory 730. In some embodiments, processor 742 can be any suitable hardware processor or combination of processors, such as a central processing unit, a graphics processing unit, etc. In some embodiments, display 744 can include any suitable display devices, such as a computer monitor, a touchscreen, a television, etc. In some embodiments, inputs 746 can include any suitable input devices and/or sensors that can be used to receive user input, such as a keyboard, a mouse, a touchscreen, a microphone, etc.

In some embodiments, communications systems 748 can include any suitable hardware, firmware, and/or software for communicating information over communication network 702 (e.g., with CLE device 710, computing device 720, etc.), and/or for communicating over any other suitable communication networks. For example, communications systems 748 can include one or more transceivers, one or more communication chips and/or chip sets, etc. In a more particular example, communications systems 748 can include hardware, firmware and/or software that can be used to establish a coaxial connection, a fiber optic connection, an Ethernet connection, a USB connection, a Wi-Fi connection, a Bluetooth connection, a cellular connection, etc.

In some embodiments, memory 750 can include any suitable storage device or devices that can be used to store instructions, values, etc., that can be used, for example, by processor 742 to present content using display 744, to communicate with one or more endomicroscopy devices 710, to communicate with one or more computing device 720, etc. Memory 750 can include any suitable volatile memory, non-volatile memory, storage, or any suitable combination thereof. For example, memory 750 can include RAM, ROM, EEPROM, one or more flash drives, one or more hard disks, one or more solid state drives, one or more optical drives, etc. In some embodiments, memory 750 can have encoded thereon a server program for controlling operation of server 740. In such embodiments, processor 742 can execute at least a portion of the server program to one or more digital images, extract content and/or style features from the digital images, generate and modify a target image, cause a target image to be presented to a user (e.g., via a user interface presented by computing device 720), receive input from a user (e.g., via a user interface presented by computing device 720), etc. For example, processor 742 can execute one or more portions of process 400. In some embodiments, server 740 can be any suitable computing device or combination of devices, such as a server computer, a distributed computing system, a personal computer, a laptop computer, a tablet computer, a smartphone, etc.

In some embodiments, communication network 702 can be any suitable communication network or combination of communication networks. For example, communication network 702 can be a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. Communications links shown in FIG. 5 can each be any suitable communications link or combination of communications links, such as wired links, fiber optic links, Wi-Fi links, Bluetooth links, cellular links, etc.

Figure 8:
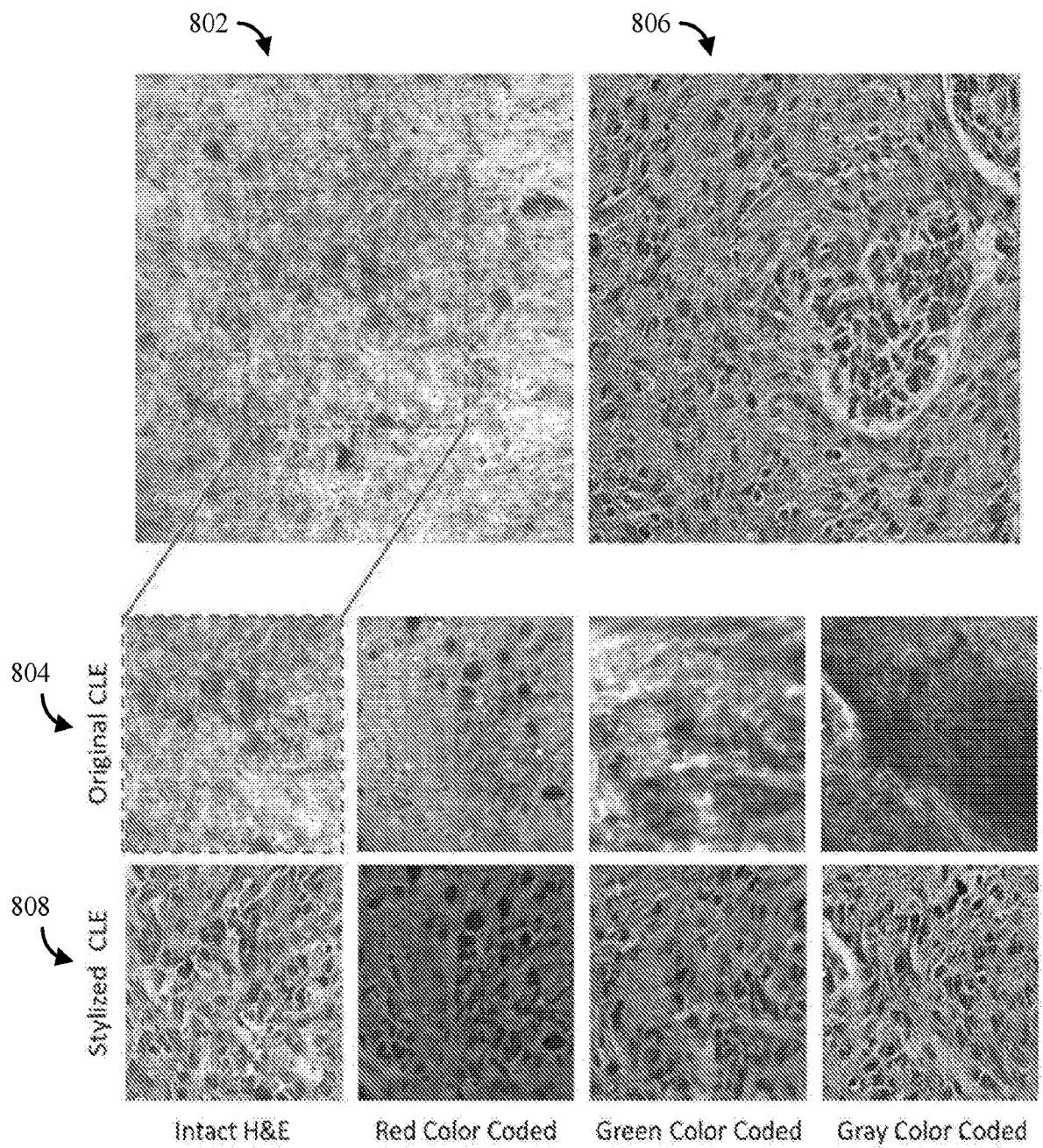
FIG. 8 shows an example of grayscale digital images generated using a confocal laser endomicroscopy device intraoperatively, a style image, and stylized versions of the original grayscale digital images created in accordance with some embodiments of the disclosed subject matter.

FIG. 8 shows an example of grayscale digital images generated using a confocal laser endomicroscopy device intraoperatively, a style image, and stylized versions of the original grayscale digital images created in accordance with some embodiments of the disclosed subject matter. Mechanisms described herein were used to generate stylized versions of 100 CLE images selected randomly from a set of CLE images generated from 15 subjects with glioma tumors. The 100 CLE images includes an original CLE image 802, and CLE images corresponding to center crops 804. A micrograph 806 of an H&E slide from a glioma tumor biopsy of a different subject (i.e., not one of the 15 subjects) was used as a style reference image when generating each of the stylized versions of the 100 CLE images. For each CLE image, the target image was modified over 1600 iterations, and the final version of the target image was used in an evaluation of whether the stylization process improved or degraded the usefulness of the digital image in making a diagnosis.

The stylized images that were generated from the 100 CLE images presented similar histological patterns to patterns observable in images of H&E slides and seemed to contain similar structures to those present in the corresponding original CLE images, as can be seen in the center crops 808 of stylized images that were generated from the original CLE images. Additionally, a quantitative image quality assessment was performed to rigorously evaluate the stylized images. Five neurosurgeons independently assessed the diagnostic quality of the 100 pairs of original and stylized CLE images. For each pair, the reviewers sought to examine various properties in each stylized image and provided a score for four properties based on the examination. One score reflected whether the stylization process removed any critical structures that were present in the original CLE image, and the degree to which the removal negatively impacted the quality of the stylized image. Another score reflected whether the stylization process removed any artifacts that were present in the original CLE image, and the degree to which the removal positively impacted the quality of the stylized image. Yet another score reflected whether the stylization process added new artifacts that were not present in the original CLE image, and the degree to which the addition negatively impacted the quality of the stylized image. Still another score reflected whether the stylization process amplified (e.g., added, surfaced, highlighted, etc.) any structures that were difficult to detect in the original CLE image, and the degree to which the amplification positively impacted the quality of the stylized image. Each score was an integer value from zero to six, with the following annotation associated with each score:

0: extreme negative impact;
    1: moderate negative impact;
    2: slight negative impact;
    3: no significant impact;
    4: slight positive impact;
    5: moderate positive impact; and
    6: extreme positive impact.

The evaluators were more familiar with H&E style images than with (original, non-transformed) CLE images. To attempt to disambiguate any effect that may be attributable purely to transforming the CLE images to look more like H&E style image, the 100 CLE images that were evaluated were placed into four different groups, where each group was processed to appear different, although the underlying final transformed image was used to generate each image. One group (I) of 25 images was transformed to H&E style images using mechanisms described herein, and presented without further modification. The other 75 images were transformed to H&E style images using mechanisms described herein, and then converted to grayscale images by averaging the red, green, and blue channels of the images. Of these 75, a group (II) of 25 were color-coded in green by setting the red and blue channels of the grayscale image to zero. A second group (III) of 25 images from the 75 converted to grayscale were color-coded in red by setting the green and blue channels of the grayscale image to zero. A final group (IV) of 25 images were maintained as grayscale images (note that these are grayscale images generated from the final target image, not the original non-transformed CLE images).

The images being evaluated were center-crops of each CLE image and corresponding stylized image to limit the number of structures that the physician has to evaluate to generate the various scores.

Figure 9:
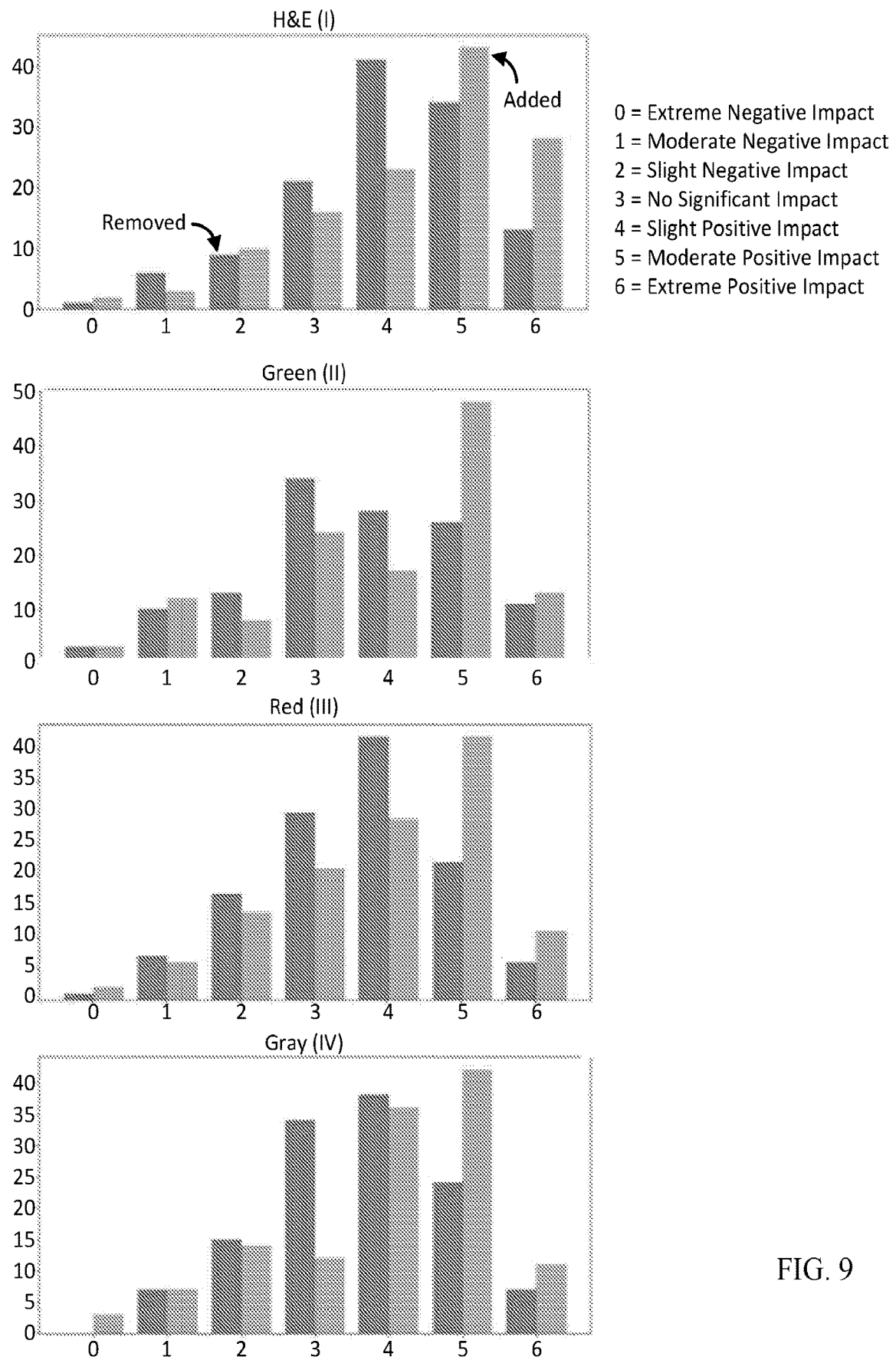
FIG. 9 shows examples of subjective impact scores given by expert reviewers for groups of sample stylized digital images transformed from CLE images using techniques described herein. One set of scores are indicative of how positively or negatively the removal of structures impacted the quality of the transformed images in comparison to the original images. The other set of scores are indicative of how positively or negatively the addition (and/or enhancement) of new (or previously imperceptible) structures impacted the quality of the transformed images in comparison to the original images.

FIG. 9 shows examples of subjective impact scores given by expert reviewers for groups of sample stylized digital images transformed from CLE images using techniques described herein. The scores were generated based on the review process described above in connection with FIG. 8. Each score is associated with two bars. The bars on the left of the pair associated with each score are indicative of how positively or negatively the removal of structures impacted the quality of the transformed images in comparison to the original images. The bar on the right is indicative of how positively or negatively the addition (and/or enhancement) of new (or previously imperceptible) structures impacted the quality of the transformed images in comparison to the original images. Note that the histograms shown in FIG. 9 aggregate all reviewers' scores across the 100 CLE images. Accordingly, each group of 25 is associated with 250 scores, as each of the five reviewers assigned two scores to each image in the group.

Overall, the number of stylized CLE images that were scored as having higher diagnostic quality than the original images (i.e., a score greater than 3) was significantly larger than those with equal or lower diagnostic quality for both removed artifacts and added structures scores (one-way chi square test p-value<0.001). Results from stylized images that were color-coded (gray, green, red) showed the same trend for the added structures scores, indicating that the improvement was likely not a simple result of the addition of H&E style color to the CLE images.

There was significant difference between how much the model added structures and removed artifacts. For all the color-coded and intact stylized images, the average of added structures scores was larger than the removed artifacts scores (t-test p-value<0.001). This suggests that the mechanisms described herein that were used to generate the stylized images were more likely to enhance the structures that were challenging to recognize in the original CLE images, than removing undesirable artifacts.

Figure 10:
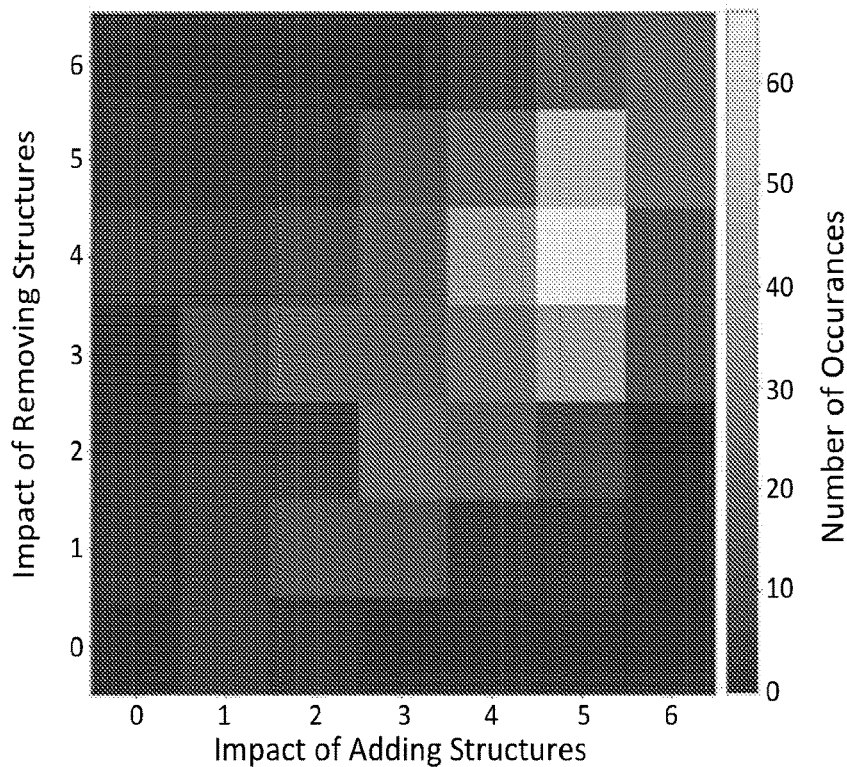
FIG. 10 shows the frequency of different combination of subjective scores for removed structures and added/enhanced structures as an intensity map.

FIG. 10 shows the frequency of different combination of subjective scores for removed structures and added/enhanced structures as an intensity map. Each block represents how many times a rater scored an image with the corresponding combination of values on the x (improvement by added structures) and y (improvement by removed artifacts) axes corresponding to that block. The most frequent incident across all the stylized images is the coordinates (5,4), which corresponds to moderately adding or enhancing structures and slightly removing artifacts, followed by (5,5) which corresponds to moderately adding or enhancing structures and moderately removing artifacts. Although the intensity maps derived from different color-coded images were not precisely the same, the most frequent combination in each group still indicated positive impact in both properties. The most frequent combination of scores, for each of the color-coded images, was as follows: intact H&E (I)=(5,4); green (II)=(5,5); red (III)=(5,4); and gray (IV)=(5,4).

As a further analysis, the number of images that had an average score below 3 was counted to see how often the mechanisms removed critical structures or added artifacts that were misleading to the evaluators. From the 100 tested images, 3 images had only critical structures removed (a score below 3 on the y-axis, and 3 on the x-axis), 4 images had only artifacts added (a score below 3 on the x-axis, and 3 on the y-axis), and 2 images had both artifacts added and critical structures removed (a score below 3 on both the x and y axes). By contrast, 84 images showed improved diagnostic quality through both removed artifacts and added structures that were initially difficult recognize (a above 3 on both the x and y axes), 6 images had only artifacts removed (a score above 3 on the y-axis, and 3 on the x-axis), and 5 images had only critical structures added or enhanced (a score above 3 on the x-axis, and 3 on the y-axis).

The results shown in FIGS. 9 and 10 indicate that style transfer with an H&E stained slide image using mechanisms described herein had an overall positive impact on the diagnostic quality of CLE images. The improvement was not solely because of the colorization of CLE images, as the stylized images that were converted to gray, red, and green were also scored as having improved diagnostic quality compared to the original CLE images.

Figure 11A:
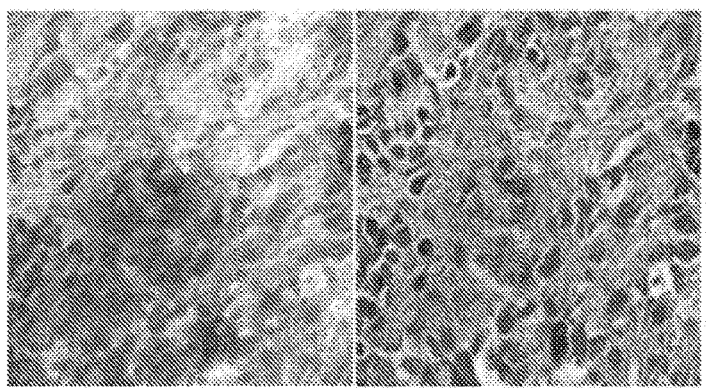
FIG. 11A shows an example of a grayscale digital image generated using a confocal laser endomicroscopy device intraoperatively and a synthetic H&E image of the original grayscale digital image in which critical structures were removed during a transformation using techniques described herein.

FIG. 11A shows an example of a grayscale digital image generated using a confocal laser endomicroscopy device intraoperatively and a synthetic H&E image of the original grayscale digital image in which critical structures were removed during a transformation using techniques described herein.

Figure 11B:
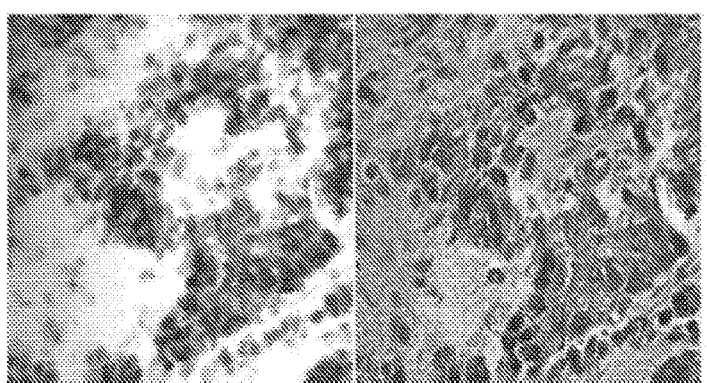
FIG. 11B shows an example of a grayscale digital image generated using a confocal laser endomicroscopy device intraoperatively and a synthetic H&E image of the original grayscale digital image in which artifacts that negatively impacted the image were added during a transformation using techniques described herein.

FIG. 11B shows an example of a grayscale digital image generated using a confocal laser endomicroscopy device intraoperatively and a synthetic H&E image of the original grayscale digital image in which artifacts that negatively impacted the image were added during a transformation using techniques described herein.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It should be noted that, as used herein, the term mechanism can encompass mechanical components, optics, hardware, software, firmware, or any suitable combination thereof.

It should be understood that the above described steps of the process of FIG. 4 can be executed or performed in any order or sequence not limited to the order and sequence shown and described in the figures. Also, some of the above steps of the process of FIG. 4 can be executed or performed substantially simultaneously where appropriate or in parallel to reduce latency and processing times.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:
1. A method for transforming a digital image generated by an endomicroscopy device into a simulated pathology image, the method comprising:
   (a) receiving a first image depicting in vivo tissue of a first subject;
   (b) generating a first plurality of features indicative of content of the first image using a first hidden layer of a pre-trained convolutional neural network trained to recognize at least a multitude of classes of common objects;

(c) receiving a second plurality of features indicative of style of a second image corresponding to features generated using a second hidden layer of the pre-trained convolutional neural network,
wherein the second image depicts a histopathology slide prepared using tissue of a second subject;
(d) generating a third image;
(e) generating a third plurality of features indicative of content of the third image using the first hidden layer;
(f) generating a fourth plurality of features indicative of a style of the third image using the second hidden layer;
(g) generating a loss value based on a loss function using the first plurality of features, the second plurality of features, the third plurality of features, and the fourth plurality of features;
(h) modifying the third image based on the loss value;
(i) repeating (e) through (h) until a threshold is met indicating that modification of the third image is complete; and
(j) causing a final version of the third image to be presented in response to the threshold being met.

2. The method of claim 1, further comprising:
determining that a current value of the loss function is different than an immediately preceding value of the loss function by less than a particular amount; and
in response to determining that a current value of the loss function is different than an immediately preceding value of the loss function by less than the particular amount, determining that the threshold is met.

3. The method of claim 1, further comprising:
determining that (e) through (h) have been repeated a particular number of times; and
in response to determining that (e) through (h) have been repeated a particular number of time, determining that the threshold is met.

4. The method of claim 1,
wherein the endomicroscopy device is a confocal laser endomicroscopy device,
wherein the first image was generated by the confocal laser endomicroscopy device during a surgical procedure, and
wherein the method further comprises:
causing the final version of the third image to be presented during the surgical procedure for evaluation by a medical provider associated with the surgery.

5. The method of claim 1,
wherein (e) comprises:
providing the third image to the pre-trained convolutional neural network; and
receiving, from the first hidden layer of the pre-trained convolutional neural network, the third plurality of features indicative of content of the third image; and
wherein (f) comprises:
providing the third image to a second pre-trained convolutional neural network trained to recognize at least the multitude of classes of common objects; and
receiving, from the second hidden layer of the second pre-trained convolutional neural network, the fourth plurality of features indicative of the style of the third image.

6. The method of claim 5, wherein the pre-trained convolutional neural network and the second pre-trained convolutional neural network have the same architecture.

7. The method of claim 6, wherein the pre-trained convolutional neural network and the second pre-trained convolutional neural network have the same parameter values.

8. The method of claim 7,
wherein the pre-trained convolutional neural network and the second pre-trained convolutional neural network are instances of a 19-layer visual geometry group (VGG-19) convolutional neural network,
wherein the multitude of classes of common objects correspond to at least a portion of the classes defined by a third party that maintains a dataset of labeled images, and
wherein the first plurality of features, and the third plurality of features are generated by a first instance of the VGG-19 convolutional neural network, and the fourth plurality of features are generated by a second instance of the VGG-19 convolutional neural network.

9. The method of claim 8, wherein the VGG-19 convolutional neural network was trained using images from the dataset of labeled images.

10. The method of claim 1, wherein the first hidden layer is a convolutional layer.

11. The method of claim 1, wherein the second hidden layer is a first rectified linear unit (ReLU) layer.

12. The method of claim 11, further comprising:
receiving a fifth plurality of features indicative of a style of the second image corresponding to features generated using a second ReLU layer of the pre-trained convolutional neural network,
wherein the second ReLU layer generates a greater number of features than the first ReLU layer; and
generating the loss value based on the second plurality of features and the fifth plurality of features.

13. The method of claim 12, further comprising:
generating a first Gram matrix based on the second plurality of features;
generating a second Gram matrix based on the fifth plurality of features; and
generating the first loss value using the first Gram matrix and the second Gram matrix.

14. The method of claim 1, further comprising:
generating the first loss value using a first loss function, the first loss function corresponding to the following expression:

$$\text{Loss}_{Total} = \frac{1}{2}\sum(C_{Content} - C_{Target})^2 + \alpha \times \sum_{i=1}^{5} w^i \times \sum (S_{Ref}^i - S_{Target}^i)^2$$

where $C_{content}$ corresponds to the first plurality of features, $C_{Target}$ corresponds to the third plurality of features, $S_{Ref}^i$ corresponds to features indicative of a style of the second image and includes $S_{Ref}^1$ corresponding to the second plurality of features, and $S_{Target}^i$ corresponds to features indicative of a style of the third image and includes $S_{Target}^1$ corresponding to the fourth plurality of features, $w^i$ corresponds to weights that control how much each of i layers of the second pre-trained convolutional neural network influence the loss value, $\alpha$ is a parameter that controls relative weights of a style portion of the loss and a content portion of the loss, and $\text{Loss}_{Total}$ corresponds to the first loss value.

15. The method of claim 14, wherein each of the weights $w^i$ are 0.2, and $\alpha$ is 100.

16. The method of claim 1, wherein the second image is an image of a hematoxylin and eosin (H&E) stained tissue sample.

17. The method of claim 16, wherein the first image depicts tissue associated with a first subject, and the second image depicts tissue extracted from a second subject.

18. The method of claim 17,
wherein the first image depicts brain tissue, and
wherein the second image depicts a portion of a glioma tumor.

19. A system, comprising:
an endomicroscopy device, comprising:
  a probe; and
  a light source,
    wherein the endomicroscopy device is configured to generate image data representing a subject's tissue during an interventional procedure; and
a computing device comprising:
  a hardware processor; and
  memory storing computer-executable instructions that, when executed by the processor, cause the processor to:
    (a) receive a first image depicting in vivo tissue of a first subject;
    (b) generate a first plurality of features indicative of content of the first image using a first hidden layer of a first pre-trained convolutional neural network trained to recognize at least a multitude of classes of common objects;
    (c) receive a second plurality of features indicative of style of a second image corresponding to features generated using a second hidden layer of the pre-trained convolutional neural network,
      wherein the second image depicts a histopathology slide prepared using tissue of a second subject;
    (d) generate a third image;
    (e) generate a third plurality of features indicative of content of the third image using the first hidden layer;
    (f) generate a fourth plurality of features indicative of a style of the third image using the second hidden layer;
    (g) generate a loss value based on a loss function using the first plurality of features, the second plurality of features, the third plurality of features, and the fourth plurality of features;
    (h) modify the third image based on the loss value;
    (i) repeat (e) through (h) until a threshold is met indicating that modification of the third image is complete; and
    (j) cause a final version of the third image to be presented in response to the threshold being met.

20. A non-transitory computer readable medium containing computer executable instructions that, when executed by a processor, cause the processor to perform a method for transforming a digital image generated by an endomicroscopy device into a simulated pathology image, the method comprising:
  receiving a first image captured by the endomicroscopy device;
  providing the first image to a first pre-trained convolutional neural network,
    wherein the first pre-trained convolutional neural network is trained to recognize at least a multitude of classes of objects;
  receiving, from a first hidden layer of the first pre-trained convolutional neural network, a first plurality of features indicative of content of the first image;
  receiving a second plurality of features indicative of a style of a second image that depicts a portion of a histopathology slide;
  receiving a third plurality of features indicative of content of a third image;
  receiving a fourth plurality of features indicative of a style of the third image;
  generating a first loss value based on the first plurality of features, the second plurality of features, the third plurality of features, and the fourth plurality of features,
    wherein the first loss value is indicative of similarity between the content of the first image and the third image and similarity between the style of the second image and the style of the third image;
  generating a fourth image by modifying values associated with one or more pixels of the third image based on the first loss value;
  providing the fourth image to the first pre-trained convolutional neural network;
  receiving, from the first hidden layer of the first pre-trained convolutional neural network, a fifth plurality of features indicative of content of the fourth image;
  providing the fourth image to a second pre-trained convolutional neural network,
    wherein the second pre-trained convolutional neural network is trained to recognize at least the multitude of classes of objects;
  receiving, from a second hidden layer of the second pre-trained convolutional neural network, a sixth plurality of features indicative of a style of the fourth image;
  generating a second loss value based on the first plurality of features, the second plurality of features, the fifth plurality of features, and the sixth plurality of features,
    wherein the second first loss value is indicative of similarity between the content of the first image and the fourth image and similarity between the style of the second image and the style of the fourth image;
  generating a fifth image by modifying values associated with one or more pixels of the fourth image based on the second loss value; and
  causing the fifth image to be presented using a display.

* * * * *

UNITED STATES PATENT AND TRADEMARK OFFICE
CERTIFICATE OF CORRECTION

PATENT NO. : 12,131,461 B2
APPLICATION NO. : 17/310305
DATED : October 29, 2024
INVENTOR(S) : Mohammadhassan Izadyyazdanabadi et al.

It is certified that error appears in the above-identified patent and that said Letters Patent is hereby corrected as shown below:

In the Specification

Column 1, Line 13, "20182019" should be --2019--.

Column 4, Line 41, "$S_{Ref}{}^i$" should be --$S_{Ref}^i$--.

Column 4, Line 43, "$S_{Ref}{}^1$" should be --$S_{Ref}^1$--.

Column 4, Line 44, "$S_{Target}{}^i$" should be --$S_{Target}^i$--.

Column 4, Line 45, "$S_{Target}{}^1$" should be --$S_{Target}^1$--.

Column 15, Line 30, "$S_{Ref}{}^i$" should be --$S_{Ref}^i$--.

Column 15, Line 31, "$S_{Target}{}^i$" should be --$S_{Target}^i$--.

Column 15, Line 35, "we" should be --$w^i$--.

In the Claims

Claim 14, Column 24, Line 49, "$S_{Ref}{}^i$" should be --$S_{Ref}^i$--.

Claim 14, Column 24, Line 51, "$S_{Ref}{}^1$" should be --$S_{Ref}^1$--.

Signed and Sealed this
Eleventh Day of February, 2025

Coke Morgan Stewart
*Acting Director of the United States Patent and Trademark Office*

Claim 14, Column 24, Line 52, "$S_{Target}{}^i$" should be -- $S^i_{Target}$ --.

Claim 14, Column 24, Line 53, "$S_{Target}{}^1$" should be -- $S^1_{Target}$ --.